United States Patent
Kumar

[11] Patent Number: 5,916,776
[45] Date of Patent: Jun. 29, 1999

[54] AMPLIFICATION METHOD FOR A POLYNUCLEOTIDE

[75] Inventor: Rajan Kumar, Robbinsville, N.J.

[73] Assignee: Sarnoff Corporation, Princeton, N.J.

[21] Appl. No.: 08/924,763

[22] Filed: Aug. 27, 1997

[51] Int. Cl.$^6$ .......................... C12P 19/34; C07H 21/04; G01N 15/06; B01J 8/04
[52] U.S. Cl. ....................... 435/91.1; 435/91.2; 435/91.5; 435/91.52; 536/24.3; 536/24.33; 536/25.3; 536/25.4; 422/63; 422/68.1; 422/149; 422/188; 422/189
[58] Field of Search .................. 536/22.1, 24.3, 536/25.3, 25.4, 24.33; 435/91.2, 91.1, 91.52, 91.5; 422/68.1, 63, 149, 188, 189

[56] References Cited

U.S. PATENT DOCUMENTS

| | | | |
|---|---|---|---|
| 4,683,202 | 7/1987 | Mullis | 435/91 |
| 5,525,494 | 6/1996 | Newton | 435/91.2 |
| 5,616,465 | 4/1997 | Lucas | 435/6 |
| 5,686,271 | 11/1997 | Mian et al. | 435/91.1 |
| 5,726,026 | 3/1998 | Wilding et al. | 435/7.21 |

OTHER PUBLICATIONS

Wu et al. The ligation amplification reaction (LAR)—Amplification of specific DNA sequences using sequential rounds of template–dependent ligation Genomics vol. 4, p. 560–569 1989.

Primary Examiner—Stephanie W. Zitomer
Attorney, Agent, or Firm—William J. Burke

[57] ABSTRACT

The nucleic acid amplification procedures of the present invention provide methods for amplification of a nucleic acid comprised of a first strand, comprising (a) using the first strand to generate copies of a second strand at a first location, (b) moving the copies of the second strand to a second location, and (c) using the copies of the second strand to generate copies of at least a portion of the first strand. Target nucleic acids used in the context of the present method include RNA or DNA, either single stranded or double stranded, using primer extension or joining-type protocols. Embodiments are set forth for automated forms of the claimed procedures.

30 Claims, 5 Drawing Sheets

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (xi) SEQUENCE DESCRIPTION: SEQ ID NO:1:

GAAGAGCCAA GGACAGGTAC                                              20

(2) INFORMATION FOR SEQ ID NO:2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (xi) SEQUENCE DESCRIPTION: SEQ ID NO:2:

CAACTTCATC CACGTTCACC                                              20

(2) INFORMATION FOR SEQ ID NO:3:

(i) SEQUENCE CHARACTERISTICS:
      (A) LENGTH: 60 base pairs
      (B) TYPE: nucleic acid
      (C) STRANDEDNESS: single
      (D) TOPOLOGY: linear (xi) SEQUENCE DESCRIPTION: SEQ ID NO:3:

CTGAATTACA TTCCCAACCG CGTGGCACAA CAACTGGCGG GCAAACAGTC GTTGCTGATT    60

(2) INFORMATION FOR SEQ ID NO:4:

(i) SEQUENCE CHARACTERISTICS:
      (A) LENGTH: 24 base pairs
      (B) TYPE: nucleic acid
      (C) STRANDEDNESS: single
      (D) TOPOLOGY: linear (xi) SEQUENCE DESCRIPTION: SEQ ID NO:4:

TTGTGCCACG CGGTTGGGAA TGTA                                        24

(2) INFORMATION FOR SEQ ID NO:5:

(i) SEQUENCE CHARACTERISTICS:
      (A) LENGTH: 26 base pairs
      (B) TYPE: nucleic acid
      (C) STRANDEDNESS: single
      (D) TOPOLOGY: linear

```
        (xi) SEQUENCE DESCRIPTION: SEQ ID NO:5:

AGCAACGACT GTTTGCCCGC CAGTTG                                                26

(2) INFORMATION FOR SEQ ID NO:6:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO:6:

TACATTCCCA ACCGCGTGGC ACAAC                                                 25

(2) INFORMATION FOR SEQ ID NO:7:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (xi) SEQUENCE DESCRIPTION: SEQ ID NO:7:

AACTGGCGGG CAAACAGTCG TTGCT                                                 25
```

AMPLIFICATION METHOD FOR A POLYNUCLEOTIDE

This invention was made with U.S. Government support under Contract No. N66001-96-C-8630. The U.S. Government has certain rights in this invention.

The present invention relates to the field of polynucleotide analysis, and, in particular, to a method whereby a single strand of a double-stranded nucleic acid is separately amplified; this method is amenable to miniaturization and automation, as disclosed herein.

Amplification of a specific segment of nucleic acid is an important component not only for the conduct of genetic research, but increasingly for the conduct of medical diagnostics, including the determination of either inborn errors of metabolism and other disorders caused by one's genetic make-up, or pathogens, such as viruses that cause AIDS and hepatitis, among others, and bacteria that cause pneumonia and diphtheria, among others. Moreover, nucleic acid amplification methods are also increasingly important for forensic evidence, wherein, for example, a perpetrator can be connected to his or her crime by correlating specific segments of nucleic acid found in samples of tissue or other biological samples (such as blood, semen, tissue scraped from a victim's fingernails, and the like) isolated from the crime scene or the victim with corresponding such segments found in the genetic make-up of a suspect.

The standard methods of nucleic acid amplification by primer extension typically entail the repeated step of denaturing the amplification products in order to conduct an ensuing round of amplification. For example, in the typical polymerase chain reaction ("PCR"), a target DNA is first denatured, usually by heat at 90° C. to 100° C., and allowed to renature in the presence of two different primers that span a region of the target nucleic acid at about 30° C. to 50° C., and which respectively are specific for the two separated strands of the DNA. A heat resistant DNA polymerase derived from thermophilic bacteria is included in a reaction mixture to extend the primers; the polymerase reaction ensues at between about 50° C. and 75° C., after which the PCR reactants are subjected to repeated cycles of denaturation (90° C. to 100° C.) followed by renaturation (30° C. to 50° C.) and extension (50° C. and 75° C.) until a prescribed level of amplification has occurred. The conventional primer extension methods require use of a thermal cycler for causing the sequential denaturations and renaturations of the nucleic acid and the amplification products (i.e., amplicons) of the amplification reaction, which can be effected manually or by an instrument. Either way, a technician is required to set up the amplification reaction, thereby incurring a substantial risk of human error in this analysis. Of course, chemical means are available for denaturing duplex nucleic acids, however a cyclic amplification process demarked by base-denaturation, for example, followed by neutralization and replenishment of reaction mix for a succeeding round of amplification will result in vastly diluted reaction products, or vastly increased time of operation due to repeated implementation of concentration protocols, such as alcohol precipitation. Another characteristic of the existing primer extension methodology is that it results in amplifying both strands of a double-stranded nucleic acid in the same reaction vessel. Existing joining-based amplifications, such as the ligase chain reaction, suffer from the same drawbacks.

Concerns regarding accuracy, including the increased potential for human error in non-automated procedures, cost of capital equipment required for thermal-based automated procedures, and the inherent difficulties posed by the chemical means alternative to thermal-based denaturation have operated to retard more widespread use of amplification procedures in medical diagnostics and forensics. Moreover, sequencing procedures would be simplified if a primer extension or joining-based amplification method similar to PCR or LCR, respectively, provided expanded populations of one strand or the other of a given nucleic acid, which can be accomplished today by special cloning procedures that provide expression of only one strand that are indeed more complicated than are the aforementioned amplification procedures.

Accordingly, there is a need for a method by which a single strand can be amplified simply and stored separately from its complement. Moreover, a need exists for an automatable method for nucleic acid amplification. Further, there is a need for a device that employs the automatable method for nucleic acid amplification. The present invention answers these needs, as set forth hereinbelow.

SUMMARY OF THE INVENTION

The present method provides a solution to the problem of reliably generating single strand amplifications of nucleic acids without having to clone the nucleic acid into a specialized plasmid. Moreover, the products of the one strand amplification methods of the present invention can be used directly for cloning and probing purposes in wide areas of forensics and molecular biology generally.

In a preferred embodiment, the present invention relates to a process for amplification of a nucleic acid comprised of a first strand, comprising (a) using the first strand to generate copies of a second strand at a first location, (b) moving the copies of the second strand to a second location, and (c) using the copies of the second strand to generate copies of at least a portion of the first strand.

DEFINITIONS

Figure 1:
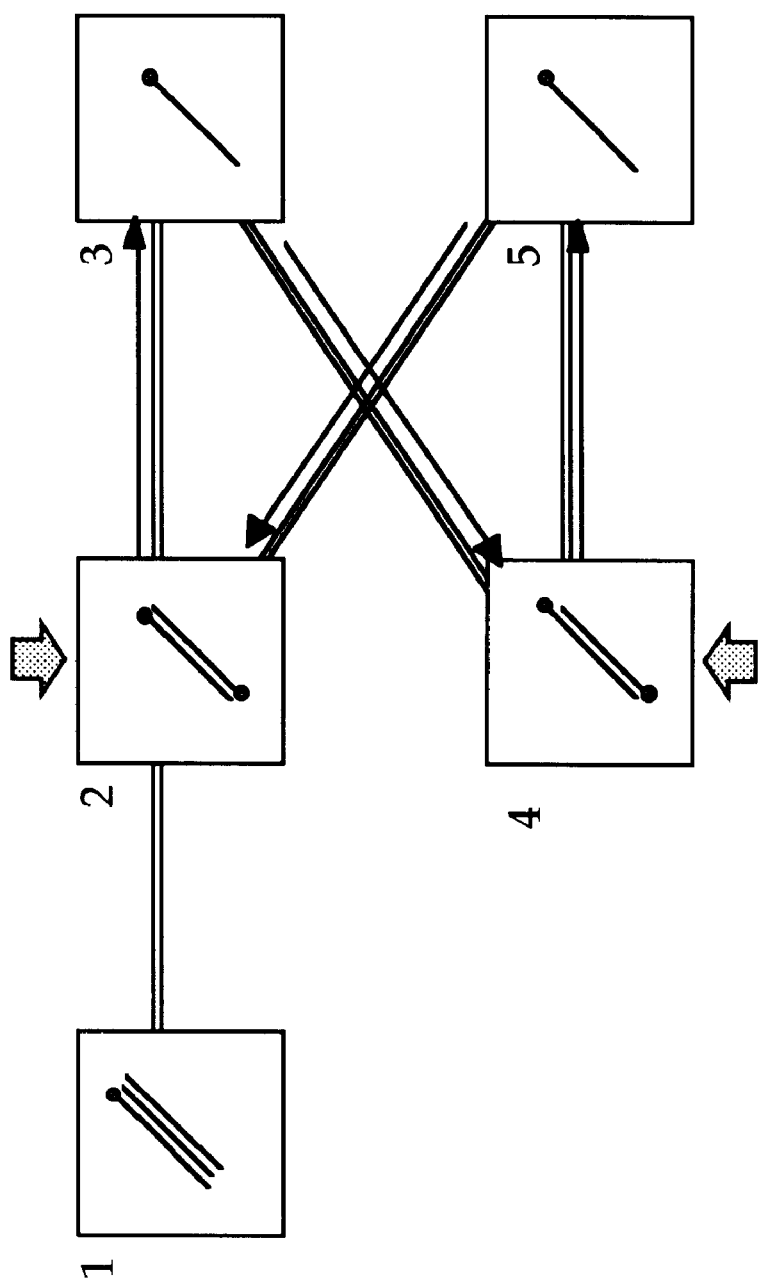
FIG. 1 depicts one embodiment of the one strand primer extension amplification method of the present invention using five locations.

The following terms shall have, for the purposes of this application, the respective meanings set forth below. In particular, for the purpose of interpreting the claims, the term definitions shall control over any assertion of a contrary meaning based on other text found herein:

"cassette" or "chemistry cassette" means a disposable device for conducting reactions therein having a cassette body, one or more upper membranes and one or more lower membranes which together define two or more chambers, including at least one supply chamber and one reaction chamber, and fluid exchange channels connecting the chambers; chambers of a cassette accommodate volumes that range from about 10 $\mu l$ to about 500 $\mu l$.

"chamber" or "fluid chamber" is a structure for containing fluids or particular matter, which structures include any reservoir or chamber, including reaction, supply, waste, metering and sample storage chambers, and other fluid-containing chambers.

"channel" or "capillary" means a conduit through which fluids pass between chambers or between a chamber and an inlet or exit of a microfluidic device; also called a "fluid exchange channel".

"chip" or "microfabricated device" means a structure having chambers and at least one reaction flow way, generally accommodating substantially smaller volumes than does a cassette; for example, chambers of a chip generally accommodate volumes that range from about 0.01 $\mu$l to about 10 $\mu$l.

"connection" or "communication" between two structures selected from chambers, inlets, channels, and capillaries are said to be "connected" or have a "route of connection" or "communicate" or are in "fluid communication" therebetween if there is one or more channels or capillaries joining the two such that fluid can move from one to the other.

"location" is a site to or at which a primer, probe, target nucleic acid, or any combination thereof can be transported, attached, or held, using, for example, magnetic substrates or direct chemical bonding; such a site can be in any sort of vessel, such as the interior of a microfluidic device, or any sort of substrate, such as a microparticle.

"microfluidic device" is a device that comprises a cassette or a chip.

"moiety" is a ligand that can be attached to a substrate, such as a microparticle, that specifically binds to another ligand, thus forming a binding pair.

"reaction chamber" means a chamber for locating reactants undergoing or to undergo a reaction, comprised of any suitable material, i.e., a material that exhibits minimal non-specific adsorptivity or is treated to exhibit minimal non-specific adsorptivity, which material can be, for example, glass, plastic, nylon, ceramic, or combinations thereof, and is connected to at least two channels for passaging material in and out of the reaction chamber; also referred to as a "first chamber".

"reaction flow-way" means a series of two or more serially connected chambers through which fluids can move, the connections for which are provided by one or more channels or capillaries.

"serially connected" refers to two or more chambers and inlet or outlet ports that are connected via channels or capillaries by which fluid from a first of the serially connected chambers or ports can pass to a second of the serially connected chambers or ports, and from there to a third of the serially connected chambers or ports, and so on until the fluid passes to the last of the serially connected chambers or ports.

"target nucleic acid" or "target" means a nucleic acid having a segment that is sought to be identified, measured, or amplified in a sample, such as a sequence intended, if present, to be amplified in a nucleic acid amplification reaction such as a polymerase chain reaction (PCR) reaction or ligase chain reaction (LCR); the target nucleic acid segment is typically part of a much larger nucleic acid molecule found in the sample.

"vessel" means a receptacle in which liquid reagents can be stored or combined, ranging in volume accommodation from milliliters, with respect to wells of a microtiter dish or an Eppendorf tube, for example, 10 $\mu$l to 500 $\mu$l, with respect to fluid chambers included in cassettes, and 0.01 $\mu$l to 10 $\mu$l, with respect to such chambers in chips.

DETAILED DESCRIPTION

The present invention relates to a method of nucleic acid amplification. In particular, the embodiments of the method disclosed herein provide at separate locations amplification of one strand or the other of a double stranded nucleic acid target that is the subject of the amplification method. Alternatively, the present method can provide amplification of the two strands of a double stranded nucleic acid target at different locations or at the same location, but collects the amplified strands separately at separate locations. In contrast, methods known in the art do not provide this feature of amplifying and/or collecting the two strands separately, such known methods including: (1) Polymerase chain reaction (PCR; see, e.g., U.S. Pat. No. 4,683,202 and *Short Protocols In Molecular Biology* (Frederick M. Ausubel et al., eds. 1992)(hereinafter, Ausubel et al.), Unit 15.1); and ligase chain reaction (LCR; see, e.g., European Patent Publication 320,308 and Schachter et al., *J. Clin. Microbiol.,* 32, 2540–2543 (1994)). Moreover, the method of the present invention is automatable, and may be used in the context of microfluidics devices disclosed in the following related applications: PCT/US97/00298, PCT/US96/17116, PCT/US96/08686, and U.S. Ser. No. 08/730,636, which are incorporated herein by reference. As set forth hereinbelow, the present invention also relates to a device that employs the aforementioned amplification method.

The present invention preferably relates to a method for amplification of a nucleic acid comprised of a first strand by which separate strands of a double-stranded nucleic acid target are amplified such that the amplified strands can be separately accumulated at different locations. The amplification procedure itself can be at one location for both strands followed by accumulating the two strands at two separate locations. Alternatively, the present method comprises (a) using the first strand to generate copies of at least a portion of the second strand at a first location, (b) moving the copies of the second strand to a second location, and (c) using the copies of the second strand to generate copies of at least a portion of the first strand. Preferably, the present method provides for the amplification of a single stranded nucleic acid and the accumulation thereof. The present method, in a second embodiment, provides for the amplification of two complementary strands of nucleic acid and the accumulation or storage of the two separate strands at separate locations. The amplification itself can be at a single location with respect to both strands, or each strand can be amplified at separate locations, the latter being prefered. It is contemplated that the target will include more nucleic acid sequences than are of interest to the requisites of a given diagnostic procedure, or that is needed to be amplified for some other procedure.

Such generation of copies of the first or second strand preferably comprises use of one or more nucleic acid-modifying enzymes; preferably the enzyme so used is a DNA polymerase, a ligase, an RNA polymerase, or an RNA-dependent reverse transcriptase, many examples and preparations of which are well-known in the art and available commercially from various sources, including Sigma Chemical Company of St. Louis, Mo. The present method includes use of such enzymes in alternative embodiments where in one embodiment a single nucleic acid-modifying enzyme is used for each round of amplification, such as, for example, a DNA polymerase or a ligase. Another embodiment includes the use of alternating enzymes in the rounds of amplification, such as using an RNA polymerase to generate RNA transcripts from a DNA template in a first round followed be an RNA-dependent reverse transcriptase in a second round to generate copy DNA therefrom, etc. Yet another embodiment includes the use of a suitable first enzyme for a determined number of rounds of amplification, such as DNA polymerase, which can serve to delimit the target that is preferably amplified, followed by the use of RNA polymerase and RNA-dependent reverse transcriptase to amplify as described above.

The present method requires use of hybridization and denaturation conditions that are well known in the art, such as those found at Ausubel et al., supra, for example. The denaturation step can use any suitable method of denaturation, such as heat, base, capacitive charging or other methods known to the art for causing nucleic acids to denature. Preferably, the present method is used along with thermal cyclers for generating cycling denaturing-renaturing/reaction temperatures for the reaction. An alternative preferred method of the present invention includes use of base for denaturation between cycles.

In one preferred embodiment of the present invention, the amplification method accommodates a fully chemical method with respect to both denaturation and joining. In addition to the chemical denaturation more fully described in PCT/US97/09663, which is incorporated herein by reference, the fully chemical embodiment of the present invention includes chemical means for joining two abutting or contiguous oligonucleotides. Such methods include the use of cyanogen bromide or carbodiimide, for example, which are used in accordance with conventional procedures. See, for example, Rubin et al., *Nucleic Acids Res.*, 23, 3547–3553 (1995); and Ng and Orgel, *Nucleic Acids Res.*, 15, 3573–3580 (1987). The fully chemical embodiment is particularly well-suited to a microfluidic environment, which is used in another embodiment of the invention, because the microfluidic environment avoids the problems stemming from evaporation as well as inconstant volumes.

Hybridization or annealing conditions used in the context of any embodiment of the present invention provided for hybridization of preferably nucleic acids having preferably at least about 80% identity with respect to the length of the primer or probe and the complementary portion of a particular target nucleic acid, more preferably at least about 85% identity, yet more preferably at least about 90% identity, even more preferably at least about 95% identity and most preferably, at least about 97% identity. As herein used, the terms "stringent conditions" and "stringent hybridization conditions" mean hybridization will occur only if there is at least about 95% and preferably at least about 97% identity between the sequences. An example of stringent hybridization conditions is overnight incubation at 42° C. in a solution comprising: 50% formamide, 5× SSC (150 mM NaCl, 15 mM trisodium citrate), 50 mM sodium phosphate (pH7.6), 5× Denhardt's solution, 10% dextran sulfate, and 20 $\mu$g/ml denatured, sheared salmon sperm DNA, followed by washing the hybridization support in 0.1× SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein. One skilled in the art knows that conditions optimal for hybridization of nucleic acids having percentage identity in the range of from about 80% to about 90% identity require lesser stringency, which commonly is attained by the lessening of temperature and/or lessening of formamide concentration.

As a general rule, the present method requires that the temperature of the reactants of an amplification procedure be maintained at certain levels for the effective and efficient use of certain enzymes used in the amplification procedure; in some embodiments, the method performs effectively at ambient room temperature, such as between about 20° C. and about 30° C. Other embodiments require the temperature of the reactants to be higher, for example up to about 75° C. However, in contrast to the methods described above, the method set forth herein is fully effective under isothermic conditions, albeit one could operate a method of the present invention using alternating temperatures, or an initial temperature at one level followed by incubation for the remainder of the procedure at a second level.

The present invention can be described with reference to locations to which reagents, polynucleotides, and substrates can be transported, which locations are generically represented as square areas in FIGS. 1–3, for example. As noted herein, the locations so represented can have any suitable shape, including random or non-random shapes that are uniform within a particular device or not, can be a vessel of any size or shape, and multiple such locations can occupy a single area. As further noted elsewhere herein, reagents, polynucleotides, and substrates included in the aforementioned locations and used in the context of the present invention are preferably transported therebetween using any suitable method of transporting such substances between locations. Preferably, as further elucidated hereinbelow, the locations referred to herein are components of a microfluidic device, however, larger structures are also contemplated as being useful devices by which to operate the methods disclosed herein. Any device having separable locations will suffice. Indeed, the method of the present invention can be performed manually or automatedly using nonmicrofluidic vessels as well, such as, but not limited to, the wells of a microtiter dish, Eppendorf tubes, and the like; or, whether a microfluidic or non-microfluidic device, the locations can be defined by magnetically positioning magnetic microparticles, for example.

As is set forth in more detail later herein, the first and second locations noted above, as well as others as is practicable for the purpose, are preferably part of a microfluidic device. Most preferably, such a microfluidic device comprises a removable chemistry cassette or a microfabricated device, i.e., a chip. Either the cassette or chip preferably comprises a first chamber that is in communication with one or more second chambers. Such first chambers preferably have a volume of from about 0.001 $\mu$l to about 700 $\mu$l, more preferably from about 0.01 $\mu$l to about 500 $\mu$l, yet more preferably from about 0.01 $\mu$l to about 250 $\mu$l.

The location at which a target or any other nucleic acid is amplified, or an amplification product, i.e., amplicons or copies of a strand or a portion of a strand of nucleic acid, is accumulated or stored is at any position in a vessel or chamber, for example. Preferably, a location, such as the aforementioned first or second location, is located at any interior place in the microfluidic device, provided that the first and second locations are not coincident.

As is further discussed below, the present method includes the use of specific binding or ligand chemistry associated with moieties that are in turn attached to a substrate, such as the interior of a microfluidic device or the external surface of a microfluidic device or vessel, more generally, or to a nucleic acid, such as a primer or a probe, such that a first or third moiety, for example, binds specifically or preferentially to a second or fourth moiety, respectively, thus forming binding pairs. Suitable binding pairs include, but are not limited to, (a) biotin and streptavidin, (b) an antigen and an antibody that specifically recognizes the antigen, (c) amine and hydrazide, (d) Protein A and an immunoglobulin G, (e)

a carbohydrate and a lectin that recognizes the carbohydrate, (f) a nucleic acid and its complement, and the like, wherein the members of each such binding pair are referred to herein as "moieties"; thus a first moiety can be, for example, biotin and a second moiety can be streptavidin, which bind to one another but neither of which bind, for example, to a third or fourth moiety, such as amine or hydrazide, for example, which, however, bind specifically to one another. Preferably, the binding pairs used for the first and the second extension products are different for applications of the present invention where it is desired that the complementary strands of the target are to be kept separate, and are the same or different where it is desired that the complementary strands of the target are to be combined. However, it is contemplated that specificity of use of the binding pair can be effected even if only one binding pair is used with respect to both first and second extension products, as when, for example, the moieties on the first extension products are allowed to bind, but the moieties on the second extension products are precluded from such binding. Such preclusion of binding can be effected using any suitable means, such as but not limited to having one or both moieties of a binding pair in the second extension product, for example, require photo activation or be blocked by a removable blocking agent, such as an antibody. Alternatively, irremovable blocking agents, such as free biotin with respect to streptavidin, can be used, in which case additional substrate with unbound moiety is supplied in subsequent steps. The chemical species of the binding pairs can be chemically linked directly to the respective probes or via a linking group as are known in the art; and, with respect to the surface that includes the corresponding chemical species of the binding pair that is included on a first or second primer, it too can be linked directly or by means of suitable linking groups. Preferably, the chemical species of the binding pairs, or the linking groups if such are employed, or both, include cleavable sites such that the binding chemistries can be separated from the first or second extension product, thus releasing free first or second extension product for use as a probe or an object of cloning, for example. Such cleavable attachments are well known in the art.

A first preferred embodiment of the present invention includes use of an enzyme that is a DNA polymerase, RNA polymerase, or reverse transcriptase, or suitable fragments thereof, or a combination thereof, as discussed above. Such suitable polymerases and fragments thereof include, but are not limited to, *E.coli* DNA polymerase I, Taq DNA polymerase, Klenow fragment, T7 DNA polymerase, and DNA polymerase derived from *E.coli*. Preferred polymerases or fragments thereof include Klenow fragment. Procedures using such enzymes include use of a primer that is complementary to the strand or portion thereof that is to be amplified, which primer can be complementary to a part of the target that is of interest, or can be "upstream" of the portion of the target nucleic acid that is of interest, i.e., is complementary of a position that is 3' of the portion of interest of the target. The method used in this first embodiment includes primer extension as the method of amplification, such as occurs in PCR procedures known in the art, and is referred to herein generically as the one strand primer extension embodiment of the present invention.

FIG. 1, which is used to illustrate one example of the one strand primer extension embodiment of the present invention, sets forth the method of the present invention in the context of a device having at least two locations, and more preferably at least five locations, which are in fluid communication as shown. Chambers 1–5 shown in FIG. 1, accordingly, represent generic locations, which can be contained within a single chamber or other vessel, or in separate chambers or vessels. The following general steps can be defined with respect to the first preferred embodiment of the invention using FIG. 1, as follows:

At location 1, a first primer is preferably annealed to a target nucleic acid, to which is added a polymerase and nucleotide triphosphates under conditions appropriate for polymerase activity, resulting in the generation of a first extension product. Preferably, the first primer has attached thereto a first moiety, as further set forth below. The first extension product is itself a target-dependent complementary target, which preferably is denatured, i.e., separated from its complementary nucleic acid. The series of actions required for polymerase activity, i.e., adding polymerase, nucleotide triphosphates, and establishing appropriate conditions therefor, are collectively referred to herein as "extension" or "extending" or "extended". The first extension product can be relocated to a second location, symbolized as location 2 in FIG. 1, whereat the first extension product can be held in place due to, for example, magnetic or chemical properties of the first moiety included with the first extension product that interacts with a magnetic field or a second moiety present at location 2, where the first and second moiety bind to one another in a reversible or irreversible manner, forming a binding pair, which is further discussed below. The second moiety alternatively can initially be present at location 1, there bind to the first moiety, forming the binding pair, and then providing suitable characteristics to the first extension product such that it can be transported from location 1 to location 2, as when, for example, the second moiety is also attached to a microparticle that is suitable for movement through a channel, particularly a microparticle that is magnetic, preferably paramagnetic, most preferably superparamagnetic, so that the first extension product can be directed to move from one location to another by action of movement or activation of a magnet or series of physically separated electromagnets that are activated in sequence along a directional vector, for example.

Exponential amplification (also referred to herein as "exponential cycling") can be effected by cycling the extension process in the context of the embodiment portrayed in FIG. 1, for example, as follows: In the first stage, the first extension product preferably anneals to a second primer at the second location (denoted by the "2" adjacent to the box), whereupon the second primer is extended, thus generating a second extension product. The second primer preferably includes a third moiety that is able to bind a fourth moiety. The fourth moiety preferably does not bind to the first or second moiety, however, it is preferably attached to a surface, such as the interior surface of a vessel, more preferably of a chamber, or a microparticle, as described further herein.

The second stage of exponential cycling includes denaturing the first extension product from the second extension product, followed by the removal of the second extension product from the second location. The second extension product can be transported using any suitable means, such as set forth hereinabove, to a third location used as a "holding chamber", for example, for the second extension product; in addition or in the alternative, the second extension product can be transported therefrom to the first location or, more preferably, to a fourth location, where more first primers are added for further extension, thus generating additional first extension product. Alternatively, a third primer can be added at the first or fourth location for extension, thus generating a third extension product, provided that the target or second extension product includes a nucleic acid sequence that is complementary to the third primer.

The third stage of exponential cycling includes denaturation of the second extension product from the first or third extension product at the first or fourth location, followed by removal of the first or third extension product therefrom. The first extension product is then preferably transported to a fifth location for holding of such product, or to the second location to provide more targets for extension from the second primer. The third extension product can be transported to the second or fifth locations as well, or, in the alternative, can be transported and captured as a sixth location (not shown) for holding such product.

Generally, all targets and extension products are preferably releasable from the chemistry by which they are captured and moved from location to location. If required for a particular purpose, first and second or third extension products can be annealed to obtain double-stranded targets. Preferably, single-stranded extension products remain single-stranded for use as probes, objects of strand-defined sequencing as known in the art, and the like.

More particularly, the preferred first embodiment, described with particular reference to FIG. 1, comprises the following steps: A sample containing the target is preferably added to location 1. Either DNA or RNA can be used as targets in this step, including where the DNA is copy, genomic, or synthetic DNA and the RNA is ribosomal, transfer, messenger, or synthetic RNA, and can include extraordinary nucleotides, such as, but not limited to, tritiated, dideoxy, or other such analogs, and further can include proteinaceous, carbohydrate, or other non-nucleic acid components. This range of possible targets applies not only to the preferred first embodiment being discussed at present, but also for all other embodiments of the present invention disclosed herein.

A first primer complementary to the target is added at location 1 and conditions sufficient for annealing of the first primer to the target are applied. Such conditions require denaturation of the target followed by appropriate salt and temperature conditions that promote and actualize hybridization between complementary nucleic acids, as are known in the art. Preferably, stringent hybridization conditions are used, as set forth hereinabove; however, one skilled in the art can reduce the temperature and/or the formamide concentration if percentage identity of the prefered annealed strands is less than about 95% identity.

Continuing in this description of one embodiment of the one strand primer extension embodiment of the present method, the annealed first primer is then extended with DNA polymerase or RNA polymerase for DNA targets, and with reverse transcriptase for RNA targets, thus forming first extension products. A step to wash unannealed first primer from location 1 is preferably also included, either before or after the primer extension, so that when, in the next step, newly formed first extension products are moved into location 2, unextended primers are not moved as well. The first extension products are preferably immobilized at location 2.

A second primer that includes a nucleotide sequence that is complementary to the 3' end of the first extension product, such that the 5' end of the second primer hybridizes to the first extension product and is available for extension, is preferably added to location 2 and allowed to anneal to the first extension product, and be extended by the addition of DNA or RNA polymerase, as appropriate, and other components sufficient for extension, as is known in the art. Such other components include, for example, 1 mM to about 10 mM $MgCl_2$, about 50 mM KCl, about 10 mM Tris-Cl, pH 8.4, about 100 µg/µl gelatin, about 2 mM of each nucleoside triphosphate, about 50 pmol of primer, about 1 µg of target nucleic acid, and about 0.25 U/µl of DNA polymerase. See Ausubel, supra at Section 15.1. The resulting extended second primer, i.e., the second extension product, has the same sequence and orientation as the starting target. The second extension product is then preferably moved into location 3 and then into location 4 where it is immobilized. The first primer, which is complementary to the initial target or to the second extension product, is added to location 4 and allowed to anneal to the second extension product, and is preferably thereafter extended to generate more copies of the first extension product. The resultant first extension product is then transferred to location 5 and, optimally immobilized at location 2 along with the first extension product already immobilized there. This process can be continued indefinitely, resulting in twice as much of both first and second extension products in each cycle, thus defining an exponential amplification. Alternatively, any step prior to the exponential cycling can be repeated to allow for greater than a doubling of extension product upon the completion of the first cycle of the exponential cycling. For example, first primer and extension thereof can be repeated numerous times, for example four times, such that a 2', where n=4, i.e., 16-fold, amplification can be accomplished regarding production of the second extension product upon additions of second primer and other requirements for extensions, as discussed herein and known in the art. A further alternative that can be implemented prior to or with the exponential cycling stages is to use a multiplicity of first probes such that various sites on the target can anneal to such probes if they are complementary to the various first probes; similarly, a multiplicity of second probes can be so used as well, or in the alternative.

The movement or holding of the various extension products, such as first and second extension products, between the various locations can be facilitated by any suitable means, including immobilization of one extension product at one location where that extension product is always used as template, and flowing newly formed, denatured complement away from or out of the location containing the immobilized extension product to a particular location for accumulation of the complement, for example. Another method contemplated in the context of the present invention is to attach certain members of the aforementioned chemical binding pairs to separate primers, such that primers that extend to become, for example, first extension product can be specifically bound to a surface that includes the other chemical binding species to which the binding species included with the primer specifically attaches, which binding species, or moieties, have been discussed above.

As is more fully described below, a suitable surface for this purpose is preferably the inside surface of a chamber for purposes of immobilizing a target in a chamber or the outside surface of a microparticle for purposes of either translocating the target from one chamber to another or immobilizing a target in a given chamber.

Many suitable configurations can be implemented that essentially are variations of the thus described one strand primer extension embodiment. For example, location 1 can be used in the first step to produce both first and second extension products at the same time, which are then moved to and immobilized at locations 2 and 4, respectively, thereby reducing the cycle time in half. Another location can be placed between locations 1 and 2 to immobilize first extension product, and second extension product produced at that extra location can be transferred and immobilized at location 4; and the process can continue as above. In this last case, location 4 will preferably accumulate second extension product and location 2 will accumulate first extension product. In another embodiment, location 3 and location 5 could be used to attach suitable chemistries to the extension products that allow their immobilization at the appointed locations such that only first extension product is immobilized at one location and only second extension product is immobilized at another location. As can be appreciated, the movement of the respective extension products can be accomplished by pumping or magnetic applications when used in concert with previously described features of the microfluidic systems, further described below.

It is appreciated by those skilled in the art that the initial first extension product synthesis can be performed to extend multiple primers, i.e., primers that are specific to different segments of a target DNA, for example, which are then immobilized at location 2. Location 2 thereafter can act as a source for a number of second extension products for multiple exponential cycles.

Figure 2:
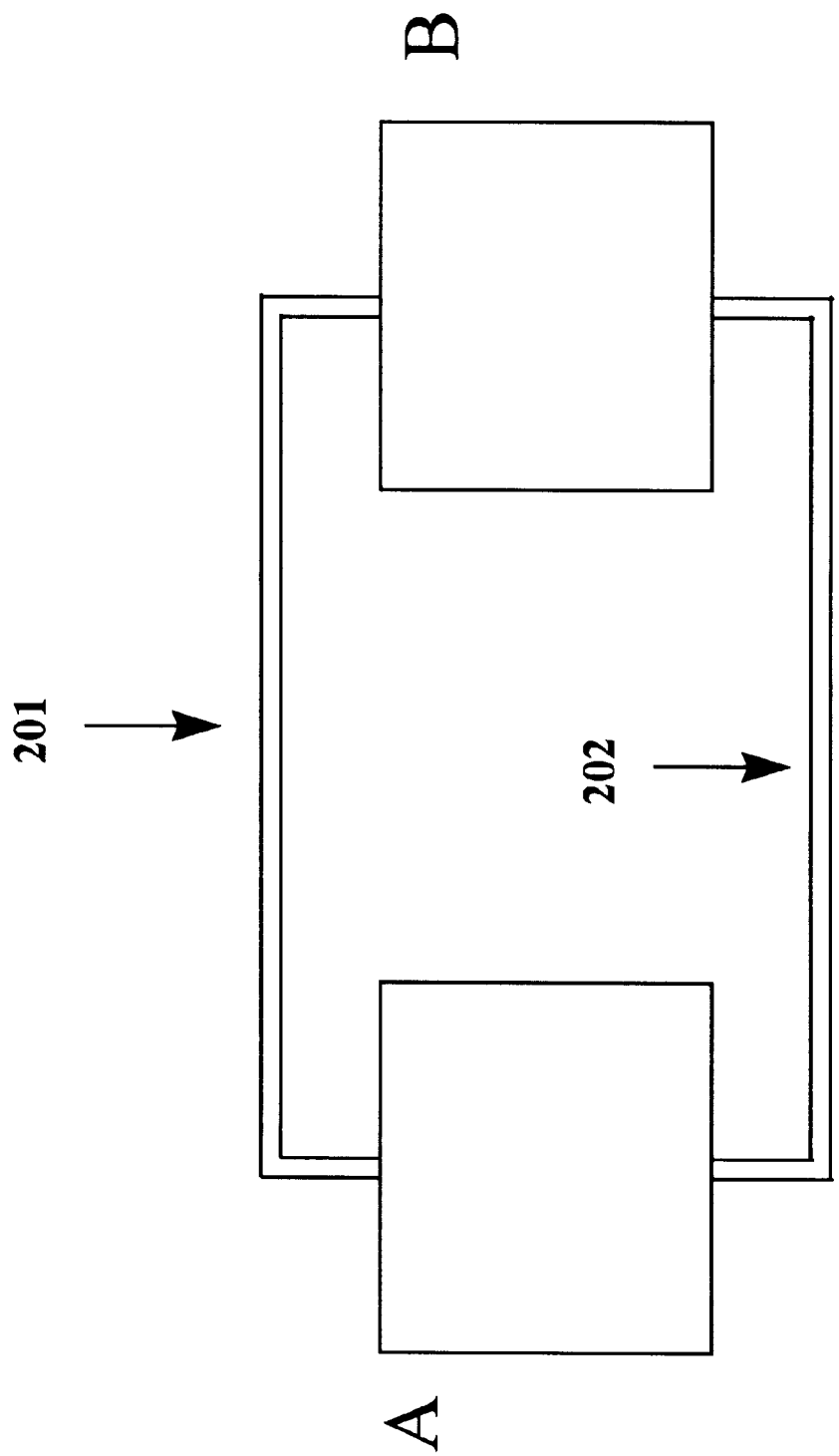
FIG. 2 depicts one embodiment of the one strand primer extension amplification method of the present invention using two locations.
Figure 3:
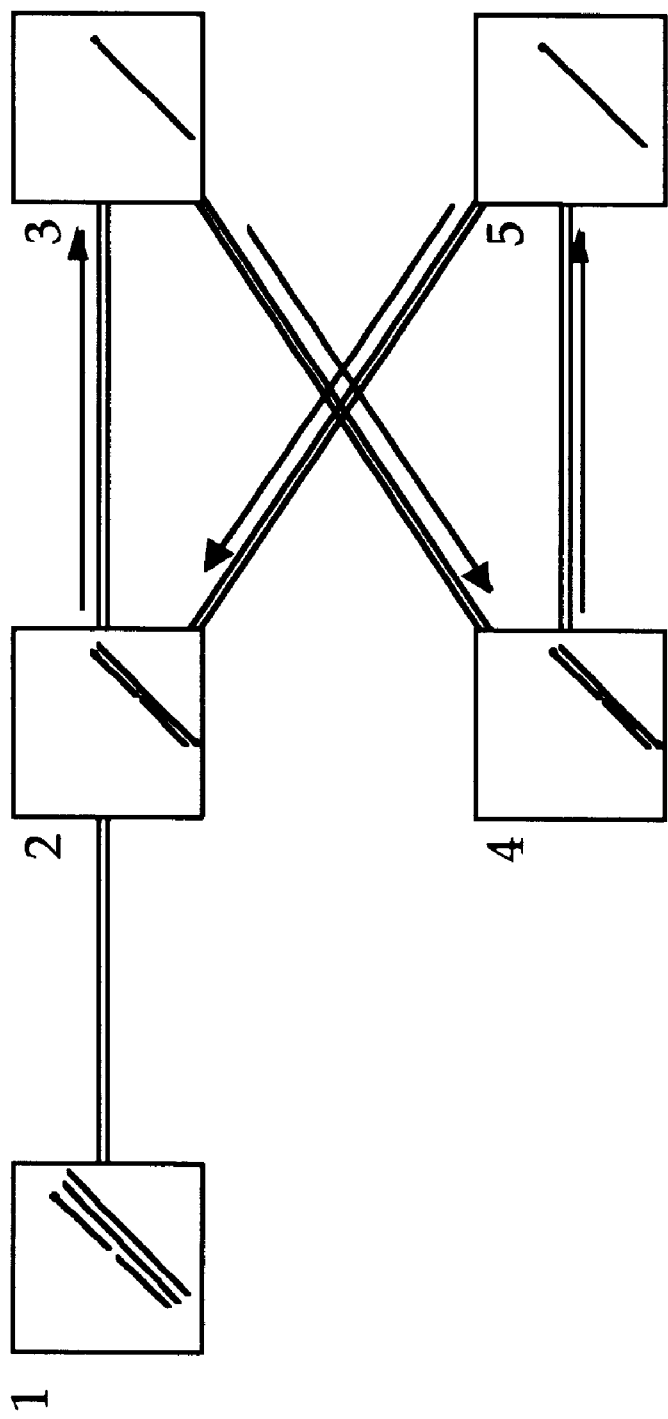
FIG. 3 depicts one embodiment of the one strand joining-based amplification method of the present invention using five locations.

The one strand primer extension amplification method just described with respect to multiple locations can also be performed using only two locations, as illustrated in FIG. 2. The two locations are respectively sites for first and second extension product amplifications, wherein first extension products are immobilized at location A and second extension products are immobilized at location B. The immobilization is preferably implemented using the aforementioned binding pairs and suitable linking chemistries for attaching the species of the binding pairs to the respective first and second primers and the surfaces by which the respective targets are held in place. The system preferably includes means for transporting in new probes and removing unused probes, and moving nascent first extension products from location B to location A, and conversely so with respect to nascent second extension products, which, if the design of FIG. 2 were for a microfluidic device, then such transporting of new and unused probes and the various extension products could be mediated by channels 201 and 202 for transport between chambers A and B, and by other such channels no shown in this particular drawing.

Figure 4:
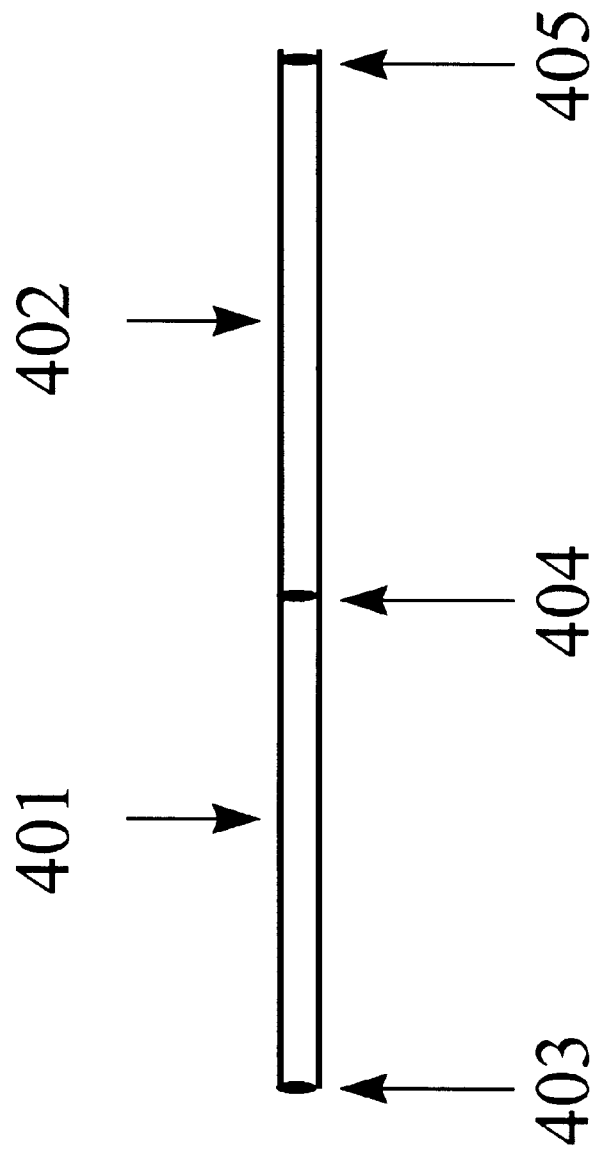
FIG. 4 depicts a microfluidic device.

A three location design is also contemplated, one exemplification of which is shown in FIG. 4, wherein a first location 404 includes immobilized target nucleic acid and is in fluid communication with other locations that provide suitable primers and other reagents needed for the primer extension embodiment (not shown). The first location 404, as the site where both strands of a target are immobilized, is suitable as the site for extension of either or both such strands. For example, a first primer that is complementary to the second strand of the target and a second primer that is complementary to the first strand of the target are added to the first location 404, in addition to suitable reagents and conditions for extension of the primers. The resultant extension products can then be immobilized in the first location 404 to increase the efficiency of each round of extension production. Once a sufficient amount of extension products are immobilized at the first location 404, which preferably will have been reached within one to three rounds of extension, then primers including appropriate substrates to provide for differential movement of the extension products of the respective primers are added, and the resultant extension products are transported such that the extension products of primer 1 are transported via channel 401 to location 403 and the extension products of primer 2 are transported via channel 402 to location 405.

Figure 5:
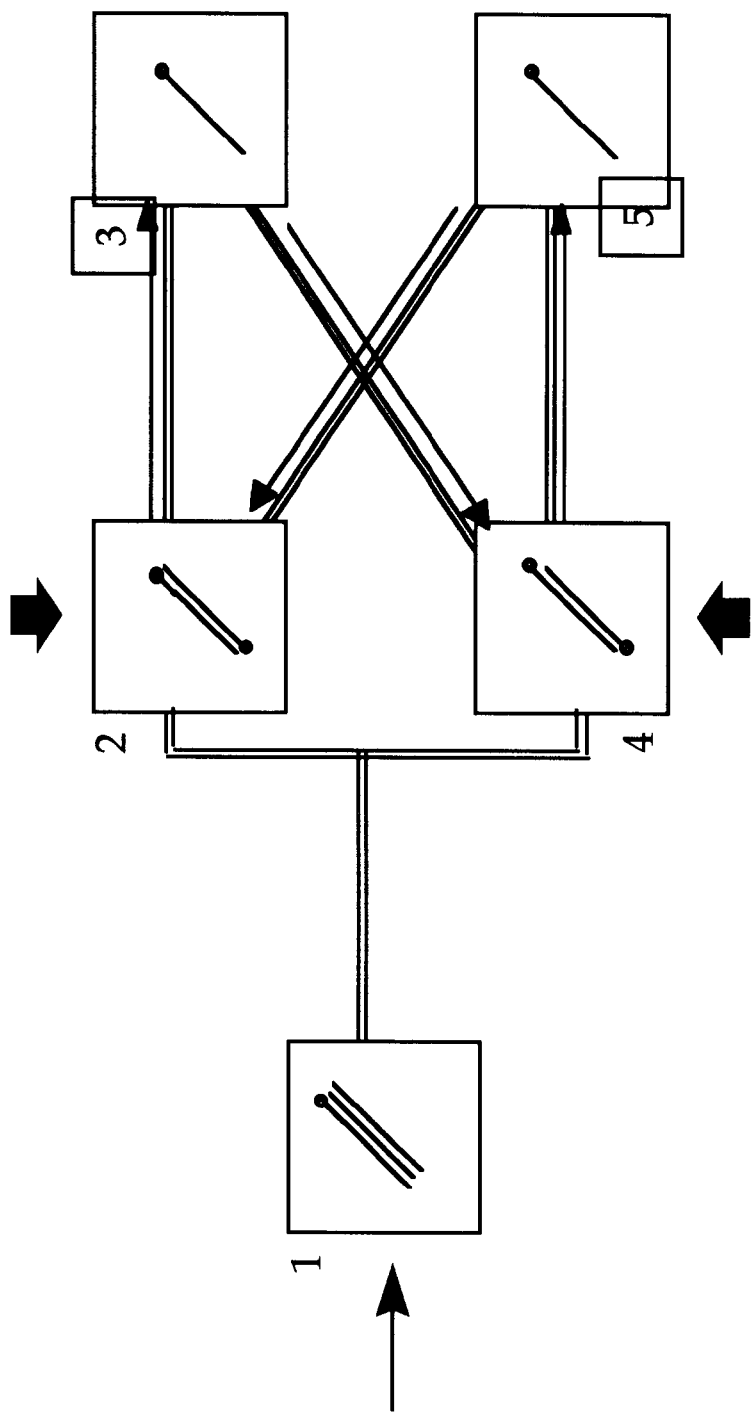
FIG. 5 depicts use of two enzymes at two separate locations, respectively.

As noted above, it is also contemplated that a primer extension amplification wherein different enzymes are used at separate locations are employed. One exemplification of this aspect of the primer extension embodiment is illustrated in FIG. 5. For example, a target nucleic acid can be introduced at location 1, where, if the target is an RNA molecule, then reverse transcriptase can be employed to generate cDNA copies thereof, and if the target is a DNA molecule, then either a DNA or RNA polymerase can be employed to generate DNA or RNA copies thereof, respectively. Presuming that the original target is an RNA, then the reverse transcripts (i.e., the cDNA) generated by the reaction of reverse transcriptase thereon are preferably transported to location 2, where the cDNA is immobilized using methods set forth herein or other conventional methods are employed, and such cDNA is then employed as the template for action of a suitable RNA polymerase in combination with suitable reagents, the introduction of which are symbolized by the arrow pointing at location 2 from above. Such transcripts are then transported to location 3, where they can be held and accumulated, or they can be transported further to location 4 and preferably immobilized therein, where they can be employed as a template for a reverse transcriptase, thus generating more cDNA using suitable reagents, the introduction of which at location 4 is symbolized by the arros ponting at location 4 from below. The cDNA is then preferably transported to location 5, where they can be held and accumulated, or they can be transported further to location 2 and immobilized therein for use as a template for the RNA polymerase previously described as being used at location 2. Thus, in this embodiment, location 2 is the site for repeated use of RNA polymerase and location 4 is the site for repeated use of reverse transcriptase.

If, alternatively, the original target is a DNA, copies of the the target can be generated using an RNA or DNA polymerase using suitable reagents, as discussed elsewhere herein, and known conventionally. If the generated copies are DNA, then such copies are preferably transported to location 2, and the exponential amplification proceeds as just described for the scenario where the original target is an RNA. If the generated copies are RNA, then such copies are preferably transported to location 4, where the reverse transcriptase discussed above can generated cDNA copies therefrom. Such copies would then be transported to location 5, and treated as discussed above, resulting in the accumulation or use as further templates of copies of the first generated copy of the original target and its complement.

Other two enzyme systems can be contemplated, as would be clear to one of ordinary skill in the art once having been apprised of this teaching. Further, three and even further numbers of different enzymes used in a polynucleotide amplification method of the present invention are contemplated as well.

More particularly, the one strand primer-extension amplification method embodiment of the present invention relates to a process for amplification of a nucleic acid having a first strand, preferably comprising (a) at the first location, associating the nucleic acid with a first primer having an attached first moiety that binds to a second moiety, thereby preferably forming a first binding pair, wherein the first primer preferably includes a nucleic acid sequence that is complementary to the first strand, preferably under conditions such that a first extension product of the first primer is synthesized, wherein the first extension product preferably is the copy of at least a portion of the second strand; and (b) at the second location, associating the first extension product with a second primer that is preferably complementary to at least a portion of the first extension product that is substantially at its 5' end, under conditions such that a second extension product of the second primer is synthesized, which second extension product preferably are copies of at least a portion of the first strand. Preferably, extension of the first and second primers is effected separately. The position at which the second primer hybridizes to the first extension product is said to be "substantially" at the 5' end thereof, meaning that at least two nucleotides remain single stranded at the 3' end of the first extension product after annealing of the second primer and first extension product. The first or second primer in one embodiment preferably comprises a multiplicity of oligonucleotides, such that different segments of a target nucleic acid can be amplified in concert, albeit only one segment of a double stranded target may be amplified with respect to both of its complementary strands. Alternatively, to provide for amplification of both complements of each segment identified or defined by the probes used, the first and second primers can both comprise a multiplicity of oligonucleotides.

Preferably, the first primer used in the context of the one strand primer extension embodiment includes the first binding pair, and the second primer has an attached third moiety that binds to a fourth moiety, thereby forming a second binding pair. It is further preferred that the first and second moieties bind to each other and not to the third or fourth moiety, and the third and fourth moieties bind to each other and not to the first or second moiety. To accommodate the movement or seizing of the primers or the extended primers, preferably the second and fourth moieties are attached to a first and second substrate, respectively. In the midst of this process, at points the first substrate is preferably separated from the second substrate, preferably wherein the first and second substrates are respectively at different locations in a microfluidic device, such as in different chambers or chambers or locations thereof. Preferably, the first and second substrates are microparticles; and such microparticles are preferably paramagnetic or superparamagnetic, wherein it is understood in the art that the former may retain a certain degree of magnetism after exposure to a magnetic field ceases such that paramagnetic beads may continue to clump in the absence of the magnetic field, whereas the latter retains no magnetic characteristic after a magnetic field is removed, allowing immediate dispersal thereafter. To accommodate differential movement of attached targets or probes, the first and second extension products or the first and second probes are respectively immobilized on microparticles having different strengths of magnetic response when subjected to a magnetic field, which can be a function qualitatively or quantitatively of the magnetic material that is included in the microparticles, as is known in the art.

In an embodiment of the one strand primer extension form of the present invention, the method preferably further comprises successively associating first and second extension products with first and second primers, respectively, under conditions sufficient for extension of the first and second primers, which are hybridized to its complement upon such extension, provided that the first and second primers hybridize at or near the 3' and 5' boundaries of the nucleic acid wherein preferably each primer hybridizes to a different extension product.

An alternative preferred embodiment of the present invention can be described as a one strand joining-based amplification method. For this embodiment, pairs of probes are used wherein a pair of probes upon hybridization to a target that includes a complementary sequence to that contained in the probes will be situated with the 3' end of one probe within a few nucleotides of the 5' end of the other probe, such that the two probes can be joined by a ligating enzyme, such as ligase or topoisomerase, or by a chemical joining agent, as discussed below. If the probes are more than about three nucleotides apart from each other, then the probes will not be joined together, unless an enzyme having the missing fill-in function is provided, such as polymerase. Accordingly, in order to treat the complementary strands separately, each pair of probes includes one probe to which is attached a member of one of the aforementioned binding pairs, such that the single probe or, preferably, the joined pair of probes can be attached to a surface thereby immobilizing the probe or joined probes thereto. As in the previous embodiment, the surface to which the probe is attached can be the inside surface of a vessel or reservoir, as in a microfluidic device, or it can be the outside surface of a microparticle, as discussed above.

This embodiment is preferably performed in the context of a microfluidic device, descriptions of which are set forth above, further below, and in certain related applications. However, this embodiment can also be performed without a microfluidic device, such as in an alternative manual or automated mode using vessels such as the wells of a microtiter dish, Eppendorf tubes, and the like. The one strand joining-based method, which is described herein with reference to FIG. 3, preferably comprises providing at location 1 a target nucleic acid, which can be DNA or RNA. A first pair of probes, named herein as "A" and "B", where the B probe has attached thereto a chemical species of one of the aforementioned binding pairs, is combined with the target nucleic acid under suitable conditions for annealing of the probes to the target nucleic acid, which will occur if the probes include sufficient complementary sequence to that of the target nucleic acid as limited by the hybridization or annealing conditions, which are discussed above. If upon annealing, the 3' end of one probe is sufficiently close to the 5' end of the other probe, the two probes are joined by a joining means added thereto, which, under suitable conditions, will join the probes together. If ligase is the joining means used, a gap of up to about three nucleotides long will be filled in and the joining will proceed. Other suitable joining means include other joining enzymes, such as topoisomerase, and use of chemical agents for joining the 3' of one nucleic acid to the 5' of another, such as cyanogen bromide or carbodiimide, for example, which are used in accordance with conventional procedures. See, for example, Rubin et al., *Nucleic Acids Res.*, 23, 3547–3553 (1995); and Ng and Orgel, *Nucleic Acids Res.*, 15, 3573–3580 (1987). Larger than 3-nucleotide gaps can be filled in using a polymerase, as known in the art.

After the joining, but before the denaturing of the probes from the target, unhybridized probe is preferably washed from the location. Preferably, the target nucleic acid is immobilized at location 1, which allows the retention of hybridized probe and the washing away of free probe. The hybridized, joined probe-target is preferably then denatured and the joined probe is removed to a location 2, where it is preferably immobilized using suitable binding pairs, for example. The target nucleic acid at location 1 can be used again to provide more joined A and B probe, while the already joined A and B probe can be used at location 2 as a second target for joining a third and fourth probe, named "C" and "D" probes, respectively, which are complementary to the A and B probes, and wherein preferably the D probe has attached thereto a moiety of one of the binding pairs, wherein preferably the binding pairs associated with the B probe differ from the binding pairs associated with the D probe such that they will not cross bind. As noted above with respect to the primer extension application method, the same binding pair can be used for both strands, such that specificity, if desired, can be achieved by selectively blocking the binding of the moieties of one strand versus the other. The procedure for amplifying using the A and B joined probe as target is identical to that just set forth with respect to the original target nucleic acid; and, in turn, again referring to FIG. 3, joined C and D probe can be moved to location 4 where the C and D joined probe can be used as a target that includes the same segment used as target as existed on the original target nucleic acid; thus, one can amplify the respective complements of the target nucleic acid. Using the differing binding pairs, and segregating the A and B joined pairs from the C and D joined pairs to separate locations, 2 and 4, respectively, wherein the joined pairs are preferably immobilized, one of skill in the art can readily perceive the exponential amplification that is provided thereby, yet always maintaining the separation of strands. Excess amplification products, i.e., the joined A-B or C-D probes, can be accumulated at locations 5 and 3, respectively.

Thus, by using the ability of the B and D probes to be captured exclusively at different locations, which location can be the inner surface of a vessel or outer surface of a microparticle, as discussed above, one preferably can segregate the joined probes from each other, and amplify exponentially.

A preferred embodiment of the one strand joining type amplification method of the present invention is employed in the context of a microfluidic device. By attaching a microparticle to the B and D probes, and using variant capture chemistries, as set forth with respect to the aforementioned binding pairs, one of skill in the art can readily appreciate that joined A and B probes and joined C and D probes can be segregated at separate locations, such as locations A and B as shown in FIG. 2, where location A binds preferentially joined A-B products and location B binds preferentially joined C-D products. Cycling of free probe and suitable reagents in suitable conditions provides for an exponential amplification of the respective joined products, which cycling of free probe and suitable reagents are mediated by, for example, channels 201 and 202.

In particular, a prefered embodiment of the one strand joining-type amplification method relates to a method for amplification of a nucleic acid comprised of a first strand, wherein the nucleic acid comprises a sequence that is complementary to a first and a second probe, the method preferably comprising: (a) adding first and second probes to the nucleic acid under conditions that are sufficient for hybridization between complementary strands of nucleic acid, and such hybridization occurs, wherein the 3' end of one and the 5' end of the other of the first and second probes are adjacent to each other upon hybridization of the first and second probes to the nucleic acid wherein the second probe includes a first moiety; (b) joining the adjacent first and second probes; (c) providing a first substrate having a second moiety, wherein the second moiety binds to the first moiety; (d) moving or holding the first substrate to or at the first location; (e) denaturing the joined first and second probes; and (f) washing unhybridized probes from the first location. The joining-type method preferably further comprises (g) at the first location, adding third and fourth probes to the joined first and second probes under conditions that are sufficient for hybridization between complementary strands of nucleic acid, and such hybridization occurs, wherein the 3' end of one and the 5' end of the other of the third and fourth probes are adjacent to each other upon the hybridization of the third and fourth probes to the joined first and second probe, wherein the fourth probes include a third moiety, and wherein the first and second probes are complementary to the third and fourth probes, respectively; (h) joining the adjacent third and fourth probes; (i) providing a second substrate having a fourth moiety, wherein the third moiety binds to the fourth moiety; (j) washing unhybridized probes from the first location; (k) denaturing the joined third and fourth probes; and (l) moving the second substrate to the second location.

More preferably, the joining type method further comprises (m) at the second location, adding first and second probes to the joined third and fourth probes under conditions that are sufficient for hybridization, and such hybridization occurs, wherein the second probes have the first moiety; (n) joining the adjacent first and second probes; (o) providing the first substrate having the second moiety, under conditions sufficient for the first and second moieties to bind; (p) washing unhybridized probes from the second location; (q) denaturing the joined first and second probes; and (r) moving the first substrate to the first location. Preferably, steps (g) through (r) are repeated.

In yet another embodiment, the present invention relates to a method for amplifying a nucleic acid, wherein the nucleic acid comprises a sequence that is complementary to a first and a second probe, the method preferably comprising: (a) attaching a target nucleic acid to a first surface at a first location; (b) combining first and second probes with the target nucleic acid under conditions that are sufficient for hybridization between complementary strands of nucleic acid, and such hybridization occurs, wherein the 3' end of one and the 5' end of the other of the first and second probes are adjacent to each other upon hybridization of the first and second probes to the target nucleic acid, and the second probe includes a first moiety; (c) joining the adjacent first and second probes; (d) washing unhybridized probes from the first location; (e) denaturing the joined probes; and (f) moving the denatured joined first and second probes from the first location. Preferably, the denatured joined first and second probes are moved to a second location having a surface having a second moiety, wherein the first and second moieties bind to each other; further comprising repeating steps (b) through (f); wherein the surface is a microparticle; wherein the microparticle is paramagnetic or superparamagnetic. In yet another preferred embodiment, the first and second locations are reservoirs of a microfluidic device; preferably, that is, the interiors of reservoirs of a microfluidic device.

Another embodiment of the present invention relates to a method for amplifying a target nucleic acid, wherein the nucleic acid comprises a sequence that is complementary to a first and a second probe, the method comprising: (a) providing the target nucleic acid attached at a first location; (b) adding first, second, third, and fourth probes to the target nucleic acid under conditions that are sufficient for hybridization between complementary strands of nucleic acid, and such hybridization occurs, wherein the 3' end of one and the 5' end of the other of the first and second probes or the 3' end of one and the 5' end of the other of the third and fourth probes are adjacent to each other upon hybridization of the first, second, third, and fourth probes to the target nucleic acid, wherein the first and second probes are complementary to the third and fourth probes, respectively, and wherein the second and fourth probes include a first moiety and a second moiety, respectively; (c) joining the adjacent first and second probes and third and fourth probes; (d) washing unhybridized probes from the first location; (e) denaturing the joined probes; and (f) moving the denatured ligated first and second probes or denatured ligated third and fourth probes from the first location. This method can further comprise using a second location having a third moiety and a third location having a fourth moiety, wherein the denatured ligated first and second probes attach to the second location and the denatured ligated third and fourth probes attach to the third location, wherein the first and third moieties and the second and fourth moieties, respectively, bind to each other. Preferably, this method further comprises repeating steps (b) through (f).

Moreover, the present method preferably further comprises (g) combining the joined probes with a first substrate having a third moiety and a second substrate having a fourth moiety, wherein the first and third moieties and the second and fourth moieties, respectively, bind to each other; and moving the bound first and second probes or the bound third and fourth probes from the first location. Preferably, both of the bound first and second probes and the bound third and fourth probes are moved from the first location to a second and a third location, respectively, wherein further the first substrate and the second substrate can be differentially moved. By differentially moved, it is intended that one substrate can be moved to one location at the same time or followed by the other substrate can be moved to a second location. Such differential movement can be accomplished by having quantitatively different magnetic attractions associated with the two substrates, where, for example, the substrates are magnetic microparticles, such that one magnetic microparticle is unaffected but the another magnetic microparticle is affected by a relatively low magnetic field as may be the case by altering the qualitative and/or quantitative characteristics of the magnetic material included with the microparticle. Microparticles can also have qualitatively different characteristics that will allow differential movement, such as having a positive versus a negative net electrical charge, or larger (for example, $10\mu$ diameter) versus smaller (for example, about $2.8\mu$ diameter) size, as examples. Such differential movement of the substrates having different nucleic acids, such as different primers or strands, also operates in the context of the primer extension embodiment of the present invention.

The joining-based embodiment of the present invention can further comprise (h) adding first and second probes and third and fourth probes to the second and third locations, respectively, under conditions that are sufficient for hybridization between complementary strands of nucleic acid, wherein the 3' end of one and the 5' end of the other of the first and second probes and the 3' end of one and the 5' end of the other of the third and fourth probes are adjacent to each other upon hybridization, and the second and fourth probes include the first moiety and the second moiety, respectively; (i) joining the adjacent first and second probes and third and fourth probes, thus forming de novo joined probes; (j) washing unhybridized probes from the second and third locations; (k) denaturing the joined probes; (l) adding unbound first and second substrates to third and second locations, respectively, wherein the unbound first and second substrates bind the de novo joined probes; and (m) moving the first substrates bound with de novo joined first and second probes to the second location or to a fourth location, and the second substrates bound with de novo joined third and fourth probes to the third location or to a fifth location. Preferably, steps (h) through (m) are repeated.

In this embodiment, the denatured joined first and second probes preferably are moved to a sixth location having a first substrate having a third moiety and the denatured joined third and fourth probes preferably are moved to a seventh location having a second substrate having a fourth moiety, wherein the first and third moieties and the second and fourth moieties, respectively, bind to each other. It is further preferred that this embodiment comprise adding first and second probes to the seventh location and third and fourth probes to the sixth location under conditions sufficient for hybridization between complementary nucleic acids; joining adjacent first and second probes and third and fourth probes, thus forming de novo joined probes; washing unhybridized probes from the sixth and seventh locations; denaturing the joined probes; and moving the denatured joined probes from the sixth and seventh positions. Preferably, the sixth and seventh locations are on an interior face of a microfluidics device. Accordingly, using the so described method, one can include moving the de novo joined first and second probes to the sixth location or to an eighth location, and the de novo joined third and fourth probes to the seventh location or to a ninth location for storing such amplification products, such that the separate strands remain separate. The method is preferably operated in the context of a microfluidics device, such that the first, second, third, fourth, fifth, sixth, seventh, eighth, and ninth locations preferably are reservoirs of a microfluidic device; some or all of the locations can be in channels, alternatively.

The primers or probes, which are used in the context of any of the embodiments discussed herein for this invention, are of any suitable length, suitability of length being a function of capability to hybridize to a unique position on target and amplicon nucleic acid, and are preferably from about 15 nucleotides to about 1000 nucleotides; more preferably, from about 20 nucleotides to about 500 nucleotides; yet more preferably, from about 20 nucleotides to about 200 nucleotides; and most preferably, from about 20 nucleotides to about 50 nucleotides. Primers or probes can be of a defined sequence of nucleotides, particularly where such information is known. Primers, but usually not probes, can be a collection of redundant primers designed by knowledge of the amino acid sequence of a protein, and application of the genetic code using methods well-known in the art, the encoding gene or mRNA for which is sought using the amplification method of the present invention.

The invention further relates to the annealing or hybridization of the primers or probes to complementary or substantially complementary target nucleic acids or amplicons (i.e., the amplified segments of nucleic acid that are the result of the present inventive method). In this regard, the invention most preferably relates to such annealing or hybridization under stringent conditions to the herein above-described polynucleotides, which conditions are set forth hereinabove.

Suitable microparticles are comprised of any suitable material, wherein a suitable material is resistant to the chemicals commonly used in nucleic acid manipulations as presented herein, such as plastic, metal, glass, and the like. Such microparticles can be of any suitable shape, including rods and beads, for example, and have a diameter of from about 0.5 $\mu$m to about 25 $\mu$m, more preferably, from about 1 $\mu$m to about 10 $\mu$m, yet more preferably from about 2 $\mu$m to about 4 $\mu$m. Preferred such microparticles include those that include paramagnetic or superparamagnetic matter, and preferably are covered by a layer of an insulator material or protein molecules that are charged positively or negatively at the reaction conditions being used, such that they react with indicator moieties, such as but not limited to a fluorescent or luminescent reporter molecules, as are known in the art.

The microparticles are attached to the primers or probes using any suitable means, including attachment via Protein Nucleic Acids (PNA; Perceptive Biosystems), biotin, avidin, streptavidin, an antigen, an antibody that recognizes the antigen, an amine, or hydrazine, among others. Preferred attachment means include biotin and streptavidin, as well as the aforementioned binding pairs.

The amplification methods disclosed herein comprise denaturing the target nucleic acid for a first cycle using any suitable means. Presuming that the target nucleic acid is DNA, the two strands of double stranded nucleic acid (referred to herein as the "W" and "C" strands) must be separated, which can be accomplished by application of heat, enzymes, or chemicals. Preferably, a nonthermal means is used, such as by application of an enzyme from the class of enzymes known as helicases or the bacterial enzyme RecA, which has helicase activity, which in the presence of riboATP is known to denature DNA. The reaction conditions suitable for separating the strands of nucleic acids with helicases are described by Kuhn et al., in *Cold Spring Harbor Symposia on Quantitative Biology, Vol. XLIII*, 63–67 (1978); techniques for using RecA are reviewed by Radding, *Ann. Rev. Genetics*, 16, 405–437 (1982). An alternative and preferred means entails the contacting of the target nucleic acid with a suitable base such that the W and C strands of the nucleic acid separate. Suitable bases include NaOH, which preferably is used at a concentration of about 0.1 M to about 0.3 M, more preferably from about 0.1 M to about 0.2 M. Other bases can be used for chemical denaturation, as is known in the art; one of ordinary skill in the art can determine empirically what a suitable concentration is using standard techniques for any given base, which concentration can be further adjusted for any given length range of nucleic acid that is used.

The present invention also relates to a device in which the aforementioned one strand method of nucleic acid amplification is employed. In particular, such a device comprises a chamber, which is a generic term that describes chambers designed for storage of fluid reagents or reactants, i.e., a supply chamber, for locating reactants undergoing a reaction, i.e., a reaction chamber, for measuring a volume of a fluid, i.e., a metering chamber, and more. More particularly, the inventive device includes a reaction chamber wherein suitable non-thermal means are employed for denaturing nucleic acid in the reaction chamber. The reaction chamber is comprised of any suitable material, wherein a suitable material is selected for its ability to be molded, heated, minimize adsorption of macromolecules, and other parameters. Suitable materials include, for example, glass, plastic, ceramic, or combinations thereof. Importantly, a reaction chamber used in the context of the present invention is connected to at least two fluid exchange channels for passaging material in and out of the reaction chamber, which is particularly important for employing chemical means of denaturation in the amplification procedure. The reaction chamber preferably remains at a constant temperature of within about two degrees centigrade, wherein the temperature is between about 20° C. and 75° C.

Preferably, the polynucleotide amplification method of the present invention is performed in the context of a microfluidic device, preferably either a cassette or a chip, the essential difference between the two being the quantity of sample and reagents used, and the sizes of the channels and chambers included therein. In certain embodiments, a chamber functions as a reaction site, referred to herein as a "first chamber". A chamber can also function as a storage site for reagents or amplified polynucleotides, or as a waste receptacle, each of which chambers are referred to herein as a "second chamber". In certain embodiments, a particular chamber can function as a site for a reaction, thus be a first chamber, yet in another step of the method as thus embodied, the same chamber can function as a waste receptacle, thus be a second chamber.

The chambers used in a cassette or chip are one or more first chambers, in which the steps relating to the amplification method can take place, although the same steps can also take place in either second chambers or channels, depending on the design used in a particular embodiment. The cassette or chip used in the context of the present invention also includes at least one second chamber, which contains reagents used in the amplification method, or are used as a receptacle for waste that results from the amplification method. Again, the same second chamber that initially was a storage facility for reagents at a prior stage of the method can serve as a waste receptacle, or as a reaction chamber, or both at varying times. Simply put, the cassette and chip design provides much latitude for design variations for placement of first or second chambers and interconnecting fluid exchange channels. Valves, both of a reversible and irreversible sort, can be used in this context, including Bursapak™-type chambers that provide their own irreversible "valve." See U.S. Ser. No. 08/664,780 and PCT/US97/00298.

More particularly with respect to the cassette used in the context of the present invention, the cassette itself can be made of any suitable material having characteristics of sufficient moldability for forming the cassette, sufficient strength and resistance to chemical attack, and the like; for example, the cassette is preferably formed of a molded plastic, such as high density polyethylene, but other materials that are suitably resistant to the chemistries used in nucleic acid identification or amplification, such as glass and silicon-based materials, can be used. Where the cassette is formed of plastic, it is preferably formed by a molding process that is used to form cavities and channels that will be sealed with upper and lower plastic films to form chambers and fluid exchange channels, such as is illustrated in FIG. 4. Such chambers A, B and C and channels 101 and 102 are formed in suitable materials, such as glass and silicon materials, by chemical etching or laser ablation. Upper and lower films typically have a thickness of from about 0.3 mils to about 5 mils, preferably from about 1 mil to about 3 mils. For chambers having a diameter of about 1 cm or more, the film thickness is more preferably about 2 mils. The first chamber C, in which the reactions relating to the amplification of the first and second strands take place, in the example hereby established by example of FIG. 4, typically has a thickness, between the upper and lower films, of from about 0.1 mm to about 3 mm, preferably of from about 0.5 to about 1.0 mm, and an area, defined by the inner surface of the upper or lower films, of preferably from about 0.05 $cm^2$ to about 2 $cm^2$, more preferably from about 0.1 $cm^2$ to about 1 $cm^2$, yet more preferably about 0.5 $cm^2$. The dimensions of the first chamber are preferably sized small enough to permit rapid throughput of fluids so that the chemical conditions of the substrates having moieties attached thereto (discussed further below) can be exchanged predictably and rapidly (on the order of from about one to about 10 seconds). Preferably, the total volume of each first chamber in a cassette is between about 5 $\mu l$ and about 250 $\mu l$, more preferably, between about 10 $\mu l$ and about 100 $\mu l$. Preferably, each first chamber has a thickness (i.e., distance between upper film and lower film) of about 1 mm or less.

Fluid exchange channels in a cassette typically describe a cylinder and have a diameter between about 200 $\mu m$ and about 500 μm; alternatively, the channels can be constructed in other shapes having a width or depth respectively of from about 200 μm to about 500 μm. Second chambers typically have a volume capacity between about 5 μl and about 500 μl, preferably from about 10 μl to about 200 μl, more preferably from about 30 μl to about 160 μl. The second chambers can contain reagents required in the amplification method, such as hybridization reagent, wash fluid, microparticles, Tris-EDTA (TE) buffer, and the like; such reagents can be contained in the second chambers in dry or liquid form, and if in dry form, can be constituted with water or other liquid reagent contained in other second chambers, or from water or other liquid reagent delivered from an external source. Second chambers used for metering a given volume preferably have a volume of about 5 μl to about 50 μl.

The upper and lower films preferably are resistant to temperatures at least as high as about 120° C. and are between about 0.5 and about 4 mils in thickness, more preferably, between about 1 and about 3 mils. The thinness of the membranes facilitates rapid heat exchange between the first chamber, or wherever the reactions to be effected within the cassette are to be located, and an adjacent heating or cooling device, which can be used to establish a constant temperature for the sample of nucleic acid being amplification, if desired.

The cassette comprising the aforementioned first chambers, second chambers, including supply, waste, and metering chambers, fluid exchange channels, and the valves and pumps further discussed previously (see Ser. No. 08/664,780, for example), can have any suitable design. Indeed, any cassette design that includes at least one second chamber, at least one first chamber, and means of communication therebetween (i.e., the fluid exchange channels) suitable for the capture of a microorganism is preferred; such a design is illustrated in FIG. 4, wherein the first chamber C is in fluid communication with second chambers A and B by means of fluid exchange channels 101 and 102; in this example, chambers A and B serve as holding chambers for accumulation of first and second strands, respectively, which are transported from the first chamber C by means of differential magnetic properties of the attached microparticles associated with one strand or the other. More preferred, the cassette comprises up to six wells for entry of a sample container and its contents, which are connected to one or more first chambers into which the sample being amplified is distributed. The surface having the molecules attached thereto can be an inside surface of the microfluidics device, such as an inside surface of a first chamber, or the surface can be microparticles as discussed above, which can be stored in second chambers.

Alternatively, the microfabricated device, i.e., the chip, used in the context of the present invention preferably includes channels or capillaries filled with fluid, wherein the channels are preferably less than about 300 μm wide and less than about 300 μm deep; more preferably less than about 200 μm width and depth; yet more preferably less than about 100 μm in width and depth. The nmicrofabricated device can be constructed of any suitable material or combination of materials, including but not limited to glass, plastic, and the like, wherein a suitable material is substantially rigid at room temperature (about 25° C.) up to at least about 40° C., and remains a solid at a temperature of up to at least about 120° C. In addition to the channels included in the microfabricated device, a preferable device, as illustrated in FIG. 4, comprises a first chamber and one or more second chambers that are interconnected by the channels. FIG. 4 provides an illustration of a microfluidic device irrespective of size distinction between a chip and a cassette as set forth hereinabove. The first chamber is alternatively referred to as the reaction chamber, however, one of the advantages of the present method is the ability to use any chamber or any channel or portions thereof as the site of the steps needed for amplifying the polynucleotide of interest, as further discussed below. The second chambers are alternatively referred to as holding, supply or waste chambers. The aforementioned material from which the chip is constructed can vary at or about the chambers, such as, for example, including at least one deformable wall at a chamber, preferably a second chamber. Preferably, the chip has at least two second chambers that have a deformable wall.

The first chamber of a chip preferably has dimensions of from about 1500 μm to about 10 μm wide, from about 1500 μm to about 10 μm long, and from about 5 μm to about 500 μm deep. More preferably, the first chamber has dimensions of from about 1000 μm to about 100 μm wide, from about 1000 μm to about 50 μm long, and from about 10 μm to about 100 μm deep. Yet more preferably, the first chamber has dimensions of from about 1000 μm to about 500 μm wide, from about 1000 μm to about 70 μm long, and from about 20 μm to about 50 μm deep. The volume capacity of the first chamber of a chip is preferably from about 0.05 μl to about 50 μl; more preferably, from about 0.1 μl to about 10 μl; yet more preferably from about 0.1 μl to about 1 μl.

The second chambers have any suitable volume such that sufficient reagents and waste chambers are thereby provided in the chip for the nucleic acid amplification protocol for which the chip is designed. In most applications, volume requirements of the second chambers preferably will not exceed about 500 μl; more particularly, second chambers used for waste disposal preferably have a volume capacity of from about 200 μl to about 500 μl, whereas second chambers used for reagent storage preferably have a volume capacity of from about 50 μl to about 250 μl.

The channels included in the chip preferably have dimensions of from about 5 μm to about 500 μm wide, from about 5 μm to about 500 μm deep, and from about 500 μm to about 250 μm long. More preferably, the channels included in the chip preferably have dimensions of from about 15 μm to about 300 μm wide, from about 10 μm to about 300 μm deep, and from about 500 μm to about 100 μm long. Most preferably, the channels have dimensions of from about 30 μm to about 150 μm wide, such as, for example, 50 μm; from about 20 μm to about 100 μm deep, such as, for example, 20 μm; and from about 500 μm to about 50 μm long.

The channels can be situated colinear or not colinear with respect to the first chamber. For example, for one embodiment that has a colinear arrangement of channels and chambers, all of the channels and chambers would be aligned in the same plane as one that is parallel with the wall of the chip. In contrast, an alternative embodiment that has a non-colinear arrangement can have a chamber situated adjacent to one wall of the chip and all or some of the channels situated adjacent to the other wall of the chip, i.e., the channels or some of the channels are situated in different planes than is at least one of the chambers. In such an embodiment, the channel would connect to a chamber by a bend away from a parallel plane with the adjacent wall, bending toward the chamber. Alternatively, channels connected to a chamber can interface the chamber such that one channel can be connected to opposite corners of, for example, a square or cube shaped chamber.

In any microfluidic device, two chambers can be situated physically adjacent to each other such that they have a common orifice through which fluid communication can occur, but which, preferably, is reversibly sealed. Alternatively, the chambers can be situated physically remote from each other, which are referred to herein as "non-touching chambers", an example of which is depicted in FIG. 4, wherein the non-touching chambers are labeled A, B, and C. Preferably, non-touching chambers are in fluid communication with each other via channels or capillaries, which are labeled 401 and 402 in FIG. 4, and which are further described below. Chambers can have any shape, including but not limited to, spheroid, cube, elliptical, and the like.

The present invention is preferably implemented in the context of a microfluidic device because such a device includes means for translocating microparticles or reagents therein, including the polynucleotide to be amplified thereby. For example, such translocations can be effected by pumping the fluid included in the device, including, but not limited to, pumping using mechanical means, such as by means of a fluid-connected syringe wherein depressing the plunger thereof creates a positive pressure inducing movement within the microfluidic device and pulling the plunger from the barrel of the syringe creates a negative pressure inducing movement within the microfluidic device in an opposite direction. Alternative methods of moving fluids and fluid contained particulate matter in the microfluidic device includes, but is not limited to, an electrode-based pump using a conductive fluid. See Ser. No. 08/838,102, for example.

As noted above, the present invention includes the translocation of microparticles in a chip or a cassette. A microparticle can have any shape, which is preferably spherical and, when spherical, is referred to as a "bead." Preferably, the microparticle has a length or diameter that does not exceed about 1 mm; more preferably less than about 500 $\mu$m; and yet more preferably, less than about 100 $\mu$m. In certain preferred embodiments, the microparticles have a maximum dimension of from about 0.5 $\mu$m to about 25 $\mu$m; more preferably from about 1 $\mu$m to about 10 $\mu$m; even more preferably, about 2 $\mu$m to about 5 $\mu$m. Beads used in the context of the present invention preferably have diameters that are less than the cross-sectional dimensions of channels when passage through the channels is preferred. The cross-sectional dimensions, such as the diameter of a cylinder, define the passage tolerance of a channel. Conversely, when a microparticle is preferably precluded from passage through the channels, the microparticle preferably has a diameter that exceeds at least one of the cross-sectional dimensions, i.e., the passage tolerance, of the channels, as further noted below.

Microparticles are comprised of any suitable material, the choice of material being guided by its characteristics, which preferably include minimal non-specific adsorptive characteristics, such as polystyrene. In other embodiments, the microparticles are comprised of, for example, glass, cellulose or a cellulose derivative, plastic, such as nylon or polytetrafluoroethylene ("TEFLON"), metal, ceramic and the like, and combinations thereof. One skilled in the art can choose materials having the characteristic of flexibility when the preferred microparticle has a length or a diameter that approximates the cross-sectional value of the capillary or channel in which the microparticle is to be employed, wherein translocation is desirable. Such flexible microparticles, despite having a diameter that is close to the passage tolerance of a capillary or channel, or even greater than the passage tolerance, can "squeeze" through the channel when caused to move due to, for example, electrode-based pumping of fluids in the microfluidic device for translocating microparticles. Conversely, a rigid material is preferred when the microparticle is only slightly larger than the channel opening and the design of the particular chip or cassette requires that the microparticles remain in a particular reservoir.

A preferred microparticle used in the context of the present invention is magnetic or responds by being seized or manipulated by a magnetic field applied to the microfluidic device, or a portion thereof. For example, magnetic particles can be localized in a particular location of a microfluidic device, such as in a chamber, by the positioning of a magnet at a proximate position, thereby keeping the microparticles from entering a channel in fluid communication thereto.

More preferably, the microparticle is paramagnetic. A paramagnetic microparticle can be comprised of, for example, iron dispersed in a polystyrene matrix, and can be obtained, for example, from Dynal (Oslo, Norway). More preferably, the microparticle is superparamagnetic as sold by Dynal (Oslo, Norway) and other commercial manufacturers. A superparamagnetic microparticle differs from a paramagnetic particle by having substantially no remanence or hysteresis. In other words, superparamagnetic microparticles respond to a magnetic field in the same fashion as paramagnetic microparticles, but whereas the paramagnetic particles exhibit some remanence and hysteresis, and therefore tend to clump together after exposure to a magnetic field ceases, superparamagnetic microparticles completely demagnetize when the field is removed, thus allowing the superparamagnetic microparticles to be redispersed without clumping immediately after the field is removed. The preferred microparticle has a moiety attached thereto. A suitable moiety provides a means for binding the microparticle to another substrate, preferably by means of a second moiety.

Another embodiment of the moiety comprises an organic or inorganic compound. Preferably, such a compound comprises an amino acid, a polypeptide, a nucleotide, a nucleoside, a nucleic acid, a carbohydrate, or an organic compound, or a combination thereof. More preferably, the moiety is a binding moiety comprising a molecule that preferentially or, yet more preferably, exclusively binds to a second molecule. Such a molecule includes, but is not limited to, avidin, biotin, streptavidin, fluorenylmethoxycarbonyl (FMOC), an antibody, a protein that binds to immunoglobulins, such as Protein A, or a lectin.

While the device is designed to allow the movement of the microparticles by pumping means, which are further discussed below, in certain embodiments and uses thereof it is preferred to hold or seize the microparticles at a certain location, or to move them as a discrete group. A preferred method for doing so includes use of magnetic microparticles, as discussed hereinabove, and requires that the device further comprise one or more magnets. Such magnets are preferably shaped and composed as disclosed in Ser. No. 08/742,971, which is incorporated herein by reference. Preferably, the magnet provides a suitable magnetic field, such as that provided by a highly magnetic permanent magnet formed of rare earths, such as those formed of the neodymium-iron-boron class of permanent magnets (available, for example, from Edmund Scientific, Barrington, N.J.). Alternatively, the magnet is an electromagnet. Either the permanent magnet or the electromagnet can be micromachined and integrated into the chip or cassette using conventional methods, as set forth by Ahn et al., *J. Microelectromech. Syst.,* 5, 151 (1996), for example.

For keeping the microparticles fixed in a given place, the passage between where the microparticles are situated and regions of the device that are in communication with that place can, for example, be narrower than the broadest dimension of the microparticles. For example, a spherical microparticle having a diameter of about 100 μm would be precluded from entering a channel having dimensions that were less than the recited diameter, particularly if the disparity of dimensions were substantial. Accordingly, a first chamber could be constructed having dimensions of 1 mm wide, 1 mm long, and 1 mm deep, containing the aforementioned spherical microparticles, and connected to channels that are substantially less than 100 μm in width and depth. By substantially less, it is preferable that the difference is at least 5%; more preferably, at least 10%; yet more preferably, at least 20%. Such a first chamber would necessarily contain the aforementioned microparticles. An alternate approach to keeping the microparticles in a fixed position requires the use of magnetic microparticles, preferably paramagnetic microparticles, more preferably superparamagnetic microparticles, and a magnet, wherein the particles are fixed at the position of the magnet. Preferably, the magnet is fixed adjacent to a reservoir, such as a first chamber, a second chamber, or a combination thereof. More preferably, the magnet is movable, such as to a location adjacent to a reservoir, such as a first chamber, a second chamber, or a combination thereof, or to a location that is not adjacent to the device. Thus, the device used in the context of the present invention has the versatility to having microparticles moved within the device or fixed in place, as per the requirements of the test for which the device is designed.

As noted above, another method of moving the microparticles or liquid reagents from position to position within the microfabricated device, is by pumping fluid within the device. Any pumping device of suitable dimensions can be used as an internal pump in the context of the microfluidics device of the invention. Such pumps can include microelectromechanical systems (MEMS), such as reported by Shoji et al., *Electronics and Communications in Japan*, Part 2, 70 52–59 (1989) or Esashi et al., *Sensors and Actuators*, 20, 163–169 (1989) or piezoelectric pumps such as described in Moroney et al., *Proc. MEMS*, 91, 277–282 (1991). Other suitable pumps work by means of, for example, hydrodynamic pressure, as set forth by Rose and Jorgensen, Analytical Chemistry, 60, 642–648 (1988); thermal energy, as set forth by Burns et al., *Proc. Natl. Acad. Sci. U.S.A.*, 93, 5556–5561 (1996); thermopneumatic force, as set forth by Shoji and Esashi, *Journal of Micromechanics & Microengineering*, 4, 147–171 (1994); piezoelectric force, as set forth by Shoji and Esashi, supra; or electrostatic force, as set forth by Shoji and Esashi, supra, using techniques well known in the art.

Preferably, the pumps used in the present invention have no moving parts. Such pumps can comprise electrode-based pumps, which are generically referred to herein as electokinetic pumps. At least two types of such electrode-based pumping has been described, typically under the names "electrohydrodynamic pumping" (EHD) and "electroosmosis" (EO). "EHD pumping has been described by Bart et al," *Sensors and Actuators*, A21–A23, 193–197 (1990) and Richter et al., *Sensors and Actuators*, A29, 159–168 (1991). EO pumps have been described by Dasgupta et al., *Anal. Chem.*, 66, 1792–1798 (1994) and Rose and Jorgensen, supra.

EO pumping is believed to take advantage of the principle that the surfaces of many solids, including quartz, glass and the like, become charged, negatively or positively, in the presence of ionic materials, such as salts, acids or bases. The charged surfaces will attract oppositely charged counter ions in solutions of suitable conductivity. The application of a voltage to such a solution results in a migration of the counter ions to the oppositely charged electrode, and moves the bulk of the fluid as well. The volume flow rate is proportional to the current, and the volume flow generated in the fluid is also proportional to the applied voltage. Typically, in channels of capillary dimensions, the electrodes effecting flow can be spaced further apart than in EHD pumping, since the electrodes are only involved in applying force, and not, as in EHD, in creating charges on which the force will act. EO pumping is generally preferred for pumping conductive solutions.

EHD pumps are generally suitable for moving fluids of extremely low conductivity, e.g., $10^{-14}$ to $10^{-9}$ S/cm. It has been demonstrated in Ser. No. 08/730,636, the contents of which are incorporated herein by reference, that a broad range of solvents and solutions can be pumped using appropriate solutes that facilitate pumping, using appropriate electrode spacings and geometries, or using appropriate pulsed or d.c. voltages to power the electrodes.

A more preferred method of pumping uses electrosmosis. Movement of fluid within the device results from the application of an electric field to the capillary or device, wherein the capillary, reservoirs and channels through or to which the microparticles are pumped are filled with a conductive buffer. Preferably, the electric field is provided by a potential of from about 100 volts to about 30,000 volts, more preferably of from about 200 volts to about 20,000 volts, yet more preferably of from about 200 volts to about 10,000 volts, even more preferably, of from about 200 volts to about 5,000 volts, wherein the potential is applied by means of electrodes located at the outside boundaries of chambers or within channels or capillaries between which the pumping is effected. Such electrokinetic methods of pumping are further discussed in the aforementioned related applications Ser. Nos. 08/556,423 and 08/645,966, which are incorporated herein by reference.

Another preferred method of pumping is effected by a reversible actuator or roller that deforms the wall of a reservoir having a deformable wall. The hardware required to form and work such an actuator or roller are well known in the art, and is disclosed in, for example, Shoji et al., *Electronics and Communications in Japan*, Part 2, 70, 52–59 (1989) or Esashi et al., *Sensors and Actuators*, 20, 163–169 (1989).

Preferably, the present amplification method is automated, such that a controller function of a computer regulates and evaluates the process of amplification, including sensing the washing away of unbound, unincorporated matter, and assessing the accumulation of amplified product. One of ordinary skill in the software engineering art, being so instructed as by this disclosed, can prepare a suitable software program to effect these functions.

The following examples further illustrate the present invention, but of course, should not be construed as in any way limiting its scope.

EXAMPLE 1

This example illustrates the one strand primer extension embodiment of the present invention using microparticles to purify the amplified extension products.

Amplification of human β-globin gene with biotinylated primer 1 (i.e., GAAGAGCCAA GGACAGGTAC [SEQ ID NO:1]) and primer 2 (i.e., CAACTTCATCC ACGTTCACC [SEQ ID NO:2]) was performed using the GeneAmplimer Beta-globin kit and all reagents contained therein (Perkin Elmer). A first reaction mix was prepared containing 10 ng of the template, primer 1, 1× amplification buffer, dNTP mix and 2.5 Units Taq polymerase. The tube was thermal cycled with one minute each at 95° C., 55° C. and 72° C. To the reaction mix, 100 µl of streptavidin-coated magnetic Dynabeads M-280 (Dynal, Oslo, Norway) were added and incubated at room temperature (about 22° C.) for ten minutes. The sample was denatured at 95° C. for one minute and using a magnetic concentrator (MPC; Dynal, Oslo, Norway), the beads containing first extension product were separated from reaction mix and rinsed. A 100 µl aliquot of α-d-biotin was added, incubated at room temperature for ten minutes and rinsed. A second reaction mix containing $^{33}$P-labeled primer 2, 1× amplification buffer, dNTP mix and 2.5 Units Taq polymerase was added and thermal cycling as above was performed. The beads was rinsed and denatured as above. The supernatant was collected and analyzed on an 8% denaturing polyacrylamide gel, using conventional procedures. The gel was visualized using a phosphor imager (Storm System, Molecular Dynamics, Calif.). A band having a mobility that indicated the expected size was observed on the gel. Accordingly, primer extension amplification was successful on first extension product after having the first extension product attached to a microparticle.

EXAMPLE 2

This example illustrates the one strand primer extension embodiment of the present invention using microparticles to purify the amplified extension products under isothermal conditions.

The procedure substantially as described in Example 1 was repeated using an isothermal protocol at 37° C. Specifically, the differences included using 1 µl Klenow polymerase (Cat. #210S; New England Biolabs, Waltham, Mass.) in place of Taq polymerase, thermal cycling was replaced by denaturation with 0.2 N NaOH, and annealing was effected by adding an equal volume of 0.2 N HCl, thereby neutralizing the reaction mix, and primer extension was performed at 37° C. The reaction products were analyzed via polyacrylamide gel electrophoresis as described in Example 1.

A band having a mobility similar to the expected size was observed on the gel. Accordingly, primer extension amplification was successful using isothermal conditions and having the first extension product attached to a microparticle.

EXAMPLE 3

This example sets forth the present invention where a first strand is repeatedly amplified as an initial step followed by exponential cycling.

The procedure described in Example 1 was performed except thermal cycling was performed five times for extension from primer 1 in place of once before. Thermal cycling for primer 2 was performed once as in Example 1. The samples were analyzed. A 4-fold higher product was observed comparing the results of this example and the procedure exemplified in Example 1.

Thus, the repetition of individual amplification steps to increase efficiency without repetition of the complete cycle was demonstrated.

EXAMPLE 4

This example illustrates generation of first extension product, immobilization of first extension product on microparticles, use of captured first extension product to generate second extension product, immobilization of the second extension product on microparticles, generation of first extension product using captured second extension product as template and repeating the process 3 times with each of the primers.

The procedure described in Example 1 was performed except it was followed by the following procedure. The supernatant from second primer extension was incubated with another aliquot of Dynabeads M-280 (Dynal, Oslo, Norway) at room temperature for 10 minutes. The beads were rinsed and the reaction mix with primer 1, 1× amplification buffer, dNTP mix and Taq polymerase was added. The sample was thermal cycled and processed by rinsing, denaturation, collection of supernatant, capture on M-280 beads, and thermal cycling with primer 2 extension mix as in Example 1. The process was continued until three extensions each were performed with primer 1 and primer 2. At each extension step, the beads with identical extension products were collected together and used as template. The reaction products were analyzed via polyacrylamide gel electrophoresis as described in Example 1.

A band having a mobility similar to the expected size was observed on the gel. Accordingly, primer extension amplification involving at least three cycles of amplification were successful.

EXAMPLE 5

This example illustrates joining based amplification of the present invention.

0.1 pmoles/µl of template oligo LCRTEMP5X (CTGAATTACA TTCCCAACCG CGTGGCACAA CAACTGGCGG GCAAACAGTC GTTGCTGATT [SEQ ID NO:3]) with biotin on 5' end was mixed with 20 µl streptavidin coated M-280 beads (Dynal, Oslo, Norway) by incubating at RT for 15 minutes, while rotating. The beads were collected and mixed with first ligation mix [oligos LCRA (TTGTGCCACG CGGTTGGGAA TGTA [SEQ ID NO:4] with 5' phosphate) and LCRBBIO (AGCAACGACT GTTTGCCCGC CAGTTG [SEQ ID NO:5] with 5' biotin), 1× pfu buffer (20 mM Tris-HCl (pH 7.5), 20 mM KCl, 10 mM MgCl$_2$, 0.1% NP40, 0.01 mM rATP, and 1 mM DTT; Stratagene, La Jolla, Calif.) and four units pfu DNA ligase (Stratagene, La Jolla, Calif.)]. One thermal cycle consisting of 92° C. for two minutes and 60° C. for three minutes was performed. Denaturation by heating to 95° C. for two minutes was performed, the supernatant was added to streptavidin coated Dynabeads M-280 and incubated at RT for ten minutes to capture the first ligation product. 100 pmoles α-d-biotin was then added to block the beads. After rinsing the beads, second ligation mix that included: (1) oligo LCRCBIO (TACATTCCCA ACCGCGTGGC ACAAC [SEQ ID NO:6], with biotin on 5' end); (2) $^{33}$P-labeled oligo LCRD (AACTGGCGGG CAAACAGTCG TTGCT [SEQ ID NO:7] with 5' phosphate), (3) 1× pfu buffer and (4) pfu DNA ligase, was added and thermal cycled as above. The beads were rinsed, denatured by heating to 95° C. for two minutes and the supernatant containing second ligation product was collected. The supernatant was attached to another aliquot of M-280 beads and used as template with the first ligation mix. These steps were continued until three ligation steps were performed with both ligation mixes. At each ligation step, the beads with identical ligation products were collected together and used. The reaction products were analyzed via polyacrylamide gel electrophoresis as described in Example 1.

A band having a mobility similar to the expected size was observed on the gel. Accordingly, joining based embodiment of the present invention was demonstrated with a three cycle procedure.

While this invention has been described with an emphasis upon certain preferred embodiments, it will be obvious to those of ordinary skill in the art that variations in the preferred composition and method may be used and that it is intended that the invention may be practiced otherwise than as specifically described herein. Accordingly, this invention includes all modifications encompassed within the spirit and scope of the invention as defined by the claims that follow the Sequence Listing.

What is claimed is:

1. A method for amplification of at least a portion of a target nucleic acid comprised of a first strand, comprising
   (a) at a first location, generating based on the first strand copies of a second strand complementary to the first strand, which copies of the second strand are, or are adapted to be, captured on a solid support,
   (b) moving the copies of the second strand to a second location either captured on the solid support or such that said copies of the second strand are captured on the solid support at the second location, and
   (c) at the second location, generating based on the copies of the second strand copies of at least a portion of the first strand.

2. The method of claim 1, wherein the copies of the first strand are, or are adapted to be, captured by a solid support, and further comprising
   (d) moving the generated copies of the first strand to the first location such that said copies of the first strand are captured on a solid support at the first location.

3. The method of claim 1, wherein generating copies of the first or second strand comprises use of at least one nucleic acid-modifying enzyme.

4. The method of claim 3, wherein only one enzyme is used.

5. The method of claim 3, wherein a first enzyme is used at the first location and a second enzyme is used at the second location.

6. The method of claim 3, wherein the enzyme is a DNA polymerase, a ligase, an RNA polymerase, topoisomerase or a reverse transcriptase.

7. The method of claim 1, wherein the generated copies of the first or second strand are attached to first or second microparticles, respectively.

8. The method of claim 7, wherein the microparticles are paramagnetic or superparamagnetic.

9. The method of claim 8, wherein the generated copies of the first and second strand are respectively attached to microparticles having different strengths of magnetic response when subjected to a magnetic field.

10. The method of claim 1, wherein the first and second locations are part of a microfluidic device.

11. The method of claim 10, wherein the microfluidic device comprises a removable chemistry cassette or a microfabricated device.

12. The method of claim 11, wherein the first or second location is located at any interior place in the microfluidic device, provided that the first and second locations are not coincident.

13. The method of claim 6, wherein the enzyme is a DNA polymerase, RNA polymerase, or reverse transcriptase.

14. The method of claim 13, further comprising:
   at the first location, annealing the target nucleic acid with one or more first primers having an attached first moiety that binds to a second moiety, thereby forming at least one first binding pair, wherein first primers include a nucleic acid sequence that is complementary to the first strand, under conditions such that at least one first extension product of the at least one first primer is synthesized, wherein the at least one first extension product is the copy of at least a portion of the second strand; and
   at the second location, annealing the at least one first extension product with one or more second primers such that at least two nucleotides remain single stranded at the 3' end of the first extension product, under conditions such that at least one second extension product of the at least one second primer is synthesized, which at least one second extension product is a copy of at least a portion of the first strand.

15. The method of claim 14, wherein the first or second primers comprise a multiplicity of oligonucleotides so that different segments of the target nucleic acid are amplified.

16. The method of claim 14, wherein a said first primer includes the first binding pair, and a said second primer has an attached third moiety that binds to a fourth moiety, thereby forming a second binding pair.

17. The method of claim 16, wherein the second and fourth moieties are attached to a first and second substrate, respectively.

18. The method of claim 17, wherein the first substrate is separated from the second substrate.

19. The method of claim 14, further comprising successively annealing first and second extension products with first and second primers, respectively, under conditions sufficient for extension of the first and second primers, which are hybridized to their complements upon such extension, provided that the first and second primers hybridize at or near the 3' and 5' boundaries of the nucleic acid wherein each primer hybridizes to a different extension product.

20. The method of claim 11, wherein the first and second binding pairs comprise (a) biotin and streptavidin, (b) an antigen and an antibody that specifically recognizes the antigen, (c) amine and hydrazide, (d) Protein A and an immunoglobulin G, (e) a carbohydrate and a lectin that recognizes the carbohydrate, or (f) a nucleic acid and its complement, provided that the first and second moieties bind to each other and not to the third or fourth moiety, and the third and fourth moieties bind to each other and not to the first or second moiety.

21. The method of claim 6, wherein the enzyme is ligase.

22. The method for amplification of at least a portion of a target nucleic acid of claim 21, further comprising:
   (1) at the first location adding (i) at least one first probe and (ii) at least one second probe which second probe includes a first moiety to the target nucleic acid under conditions that allow hybridization between complementary strands of nucleic acid, and such hybridization occurs, wherein the 3' end of one and the 5' end of the other of the first and second probes hybridize to the target nucleic acid and are adjacent to each other upon hybridization of the first and second probes to the target nucleic acid;
   (2) ligating such adjacent, hybridized first and second probes;
   (3) providing a second moiety attached to a first substrate, and binding the second moiety to the first moiety;
   (4) moving the first substrate to, or holding the first substrate at, the first location;
   (5) denaturing to separate the ligated first and second probes from the nucleic acid;
   (6) washing unhybridized probes from the first location; and
   (7) generating based on the ligated first and second probes copies of at least a portion of a strand complementary to the ligated first and second probes.

23. The method of claim 22, further comprising:
   (8) at the first location, conducting the generating of step (7) by first adding third and fourth probes to the joined first and second probes under conditions that allow for hybridization between complementary strands of nucleic acid, and such hybridization occurs, wherein the 3' end of one and the 5' end of the other of the third and fourth probes hybridize to the joined first and second probe and are adjacent to each other upon such hybridization, wherein the fourth probes include a third moiety, and wherein the first and second probes are complementary to the third and fourth probes, respectively;
   (9) completing the generating step by ligating the adjacent third and fourth probes;
   (10) providing a fourth moiety attached to a second substrate, and binding the fourth moiety to the third moiety;
   (11) washing unhybridized probes from the first location;
   (12) denaturing to separate the ligated third and fourth probes from the joined first and second probes; and
   (13) moving the second substrate to the second location.

24. The method of claim 23, further comprising:
   (14) at the second location, adding first and second probes to the joined third and fourth probes under conditions that allow hybridization, wherein first and second probes hybridize to the joined third and fourth probes, and wherein the second probes have the first moiety;
   (15) ligating the adjacent first and second probes;
   (16) providing the first substrate having the second moiety, under conditions sufficient for the first and second moieties to bind;
   (17) washing unhybridized probes from the second location;
   (18) denaturing to separate the ligated first and second probes from the joined third and fourth probes; and
   (19) moving the first substrate to the first location.

25. A method for amplifying one or more segments of a target nucleic acid, wherein the nucleic acid comprises a sequence that is complementary to a first and a second probe, the method comprising:
   (a) providing the target nucleic acid attached at a first location;
   (b) adding first, second, third, and fourth probes to the target nucleic acid under conditions that allow hybridization between complementary strands of nucleic acid, and such hybridization occurs, wherein the 3' end of one and the 5' end of the other of the first and second probes or the 3' end of one and the 5' end of the other of the third and fourth probes are adjacent to each other upon hybridization of the first and second probes or third and fourth probes to the target nucleic acid, wherein the first and second probes are complementary to a polynucleotide consisting of the third and fourth probes joined together, and wherein the second and fourth probes include a first moiety and a second moiety, respectively;
   (c) ligating or chemically joining those of the first and second probes or third and fourth probes which are made adjacent by hybridizing to the target nucleic acid;
   (d) washing unhybridized probes from the first location;
   (e) denaturing to separate the joined probes from the target nucleic acid;
   (f) moving the denatured ligated first and second probes or denatured ligated third and fourth probes from the first location to a second location; and
   (g) generating at the second location the complement of a least of portion of said moved, ligated probes.

26. The method of claim 25, wherein the method further comprises using a second location having a third moiety and a third location having a fourth moiety, wherein the denatured ligated first and second probes attach to the second location and the denatured ligated third and fourth probes attach to the third location, wherein the first and third moieties and the second and fourth moieties, respectively, bind to each other.

27. The method of claim 25, further comprising
   (h) combining the joined probes with a first substrate having a third moiety and a second substrate having a fourth moiety, binding the first and third moieties and the second and fourth moieties, respectively, and moving the bound first and second probes or the bound third and fourth probes from the first location.

28. The method of claim 27, wherein both of the joined first and second probes are moved from the first location to a second location and the joined third and fourth probes are moved from the first location to a third location, wherein further the first substrate and the second substrate can be differentially moved.

29. The method of claim 28, further comprising
(i) after step (f) adding first and second probes to the joined third and fourth probes at the third location and the third and fourth probes to the joined a first and second probes at the second location, under conditions that allow hybridization between complementary strands of the joined first and second probes and the joined third and fourth probes, wherein the 3' end of one and the 5' end of the other of the first and second probes or the 3' end of one and the 5' end of the other of the third and fourth probes are adjacent to each other upon such hybridization, and the second and fourth probes include the first moiety and the second moiety, respectively;
(j) ligating or chemically joining the adjacent first and second probes or third and fourth probes, thus forming newly joined probes;
(k) washing unhybridized probes from the second and third locations;
(l) denaturing to separate the newly joined probes from previously joined probes;
(m) at the third location binding first substrate to newly first and second joined probes and at the second location binding second substrate to newly joined third and fourth probes; and
(n) moving the first substrates bound with newly joined first and second probes to the second location or to a fourth location, and the second substrates bound with newly joined third and fourth probes to the third location or to a fifth location.

30. A method for amplifying at least a portion of a target nucleic acid, wherein the nucleic acid comprises a sequence that is complementary to a first and a second probe, the method comprising:
(a) attaching a target nucleic acid at a first location;
(b) combining first and second probes with the target nucleic acid under conditions that allow hybridization between complementary strands of nucleic acid, and hybridizing the first and second probes to the target nucleic acid so that the 3' end of one and the 5' end of the other of the first and second probes are adjacent to each other upon such hybridization, wherein the second probe includes a first moiety;
(c) ligating or chemically joining the adjacent first and second probes;
(d) washing unhybridized probes from the first location;
(e) denaturing to separate the joined probes from the target nucleic acid;
(f) moving the denatured joined first and second probes from the first location to a second location; and
(g) generating at the second location the complement of a least of portion of said moved, ligated probes.

* * * * *